(12) United States Patent
Sauter, Jr.

(10) Patent No.: US 9,327,298 B1
(45) Date of Patent: *May 3, 2016

(54) INDUCTION BASED FLUIDIC (IBF) AND HYBRID DEVICES FOR THE MOVEMENT, TREATMENT, MEASUREMENT, INTRODUCTION AND MANUFACTURING OF LIQUID/S AND OTHER MATTER

(76) Inventor: Andrew Daniel Sauter, Jr., Henderson, NV (US)

( * ) Notice: Subject to any disclaimer, the term of this patent is extended or adjusted under 35 U.S.C. 154(b) by 1673 days.

This patent is subject to a terminal disclaimer.

(21) Appl. No.: 12/009,791

(22) Filed: Jan. 22, 2008

Related U.S. Application Data

(60) Provisional application No. 60/881,532, filed on Jan. 22, 2007.

(51) Int. Cl.
*B05B 5/00* (2006.01)
*H01J 49/00* (2006.01)
*B05B 5/025* (2006.01)
*B05B 5/043* (2006.01)

(52) U.S. Cl.
CPC . *B05B 5/00* (2013.01); *B05B 5/005* (2013.01); *B05B 5/0255* (2013.01); *B05B 5/043* (2013.01); *H01J 49/00* (2013.01)

(58) Field of Classification Search
CPC ....... B01L 3/0275; H01J 49/165; H01J 49/00; B05B 5/043; B05B 5/005; B05B 5/00
USPC ............................. 422/504; 250/288; 210/656
See application file for complete search history.

(56) References Cited

U.S. PATENT DOCUMENTS

| | | | | |
|---|---|---|---|---|
| 5,111,965 | A | * | 5/1992 | Allen et al. .................... 221/281 |
| 6,079,634 | A | * | 6/2000 | Noakes et al. .................... 239/3 |
| 6,452,166 | B1 | * | 9/2002 | Enke et al. .................... 250/288 |
| 7,785,466 | B1 | * | 8/2010 | Smith ...................... 210/321.75 |

OTHER PUBLICATIONS

Sauter et al., "Nanoliters onto media: Use of electric induction", Oct. 2001, American Laboratory, pp. 40-45.*

* cited by examiner

*Primary Examiner* — Jonathan Hurst

(57) ABSTRACT

Femtoliter to milliliter volumes of one or a plurality of different fluids of varied properties, semisolids or solids are energized electrically in an inductive or optionally an inductive-conductive manner, with one or a plurality of either analogue or digital energy sources of uni or multi-polar nature using high or optionally low DC, AC or RF voltage or energy supplies in programmed, coordinated manner with other devices (e.g., pumps or all types, syringes, pipettes, capillaries, scientific instruments, etc.) using special hardware to energize and direct matter from gaussian surfaces or multiple nested gaussian surfaces to produce and optionally fly drops or optionally sprays, to targets of all types, yielding matter directed with high precision and accuracy in volumetric, spatial and temporal terms, as the matter is optionally treated, measured, metered via current, optical, thermal or other measurement technologies with feedback, one or N channels at a time creating a digital record.

21 Claims, 52 Drawing Sheets nL dispensing, treatment device

Figure 2 Version 1.0 of circuit one, of the digital nanoliter cool-wave.

Figure 3. Version 2.0 of driving circuit of the digital nanoliter cool-wave.

Figure 4. Version 2.0, of driving circuit of the digital nanoliter cool-wave alternate view.

Figure 5 IBF Nanoliter Circuit Version 3.0 with fast 3 msec relay

Figure 7 Side view of nanoliter digital wave board Version 3.0

RF/DC, Bipolar Systems

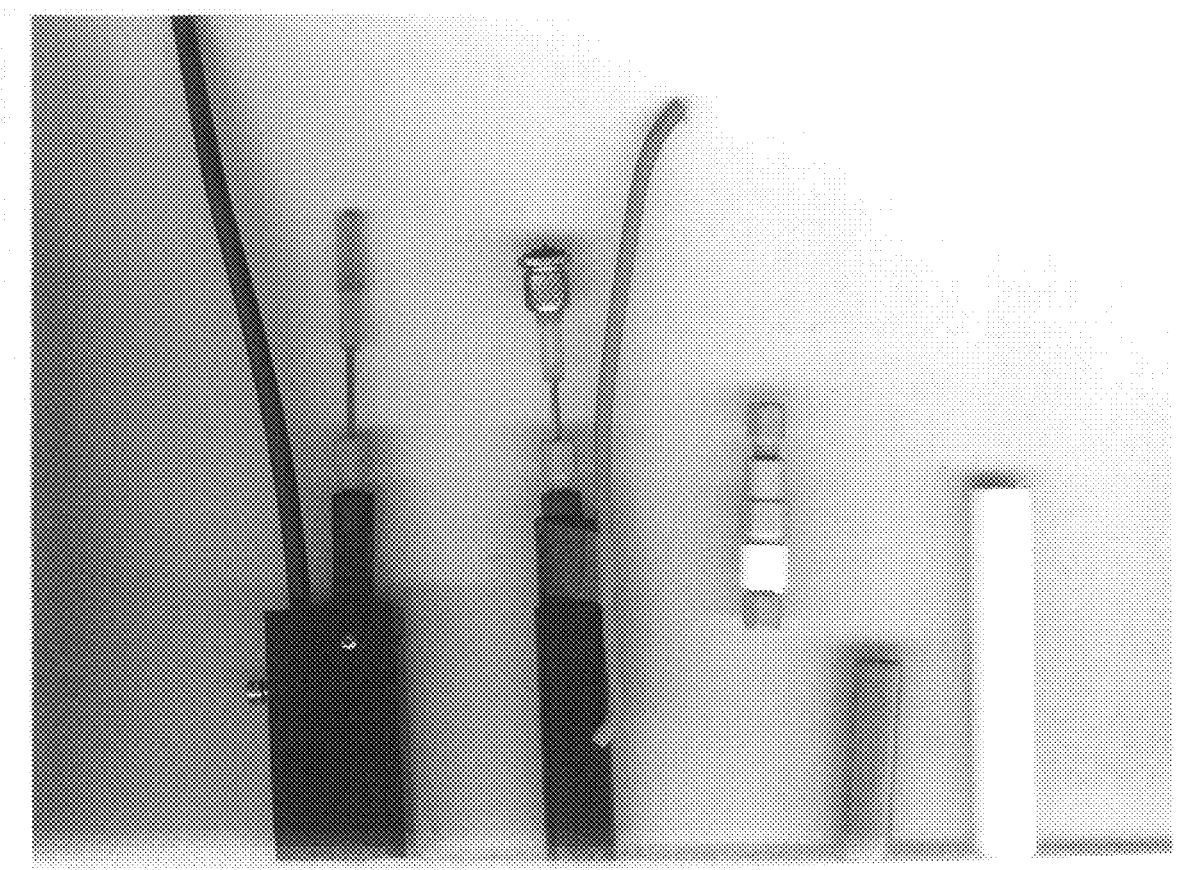
Figure 9. Two fluidic inductors and parts including starting from the rightmost, EMI/RFI shield cylindrical; cylindrical conductor; Upchurch union with union; assembled inductor with Spark Holland needle adapter and HV connection with shields and another inductor of different internal geometry.

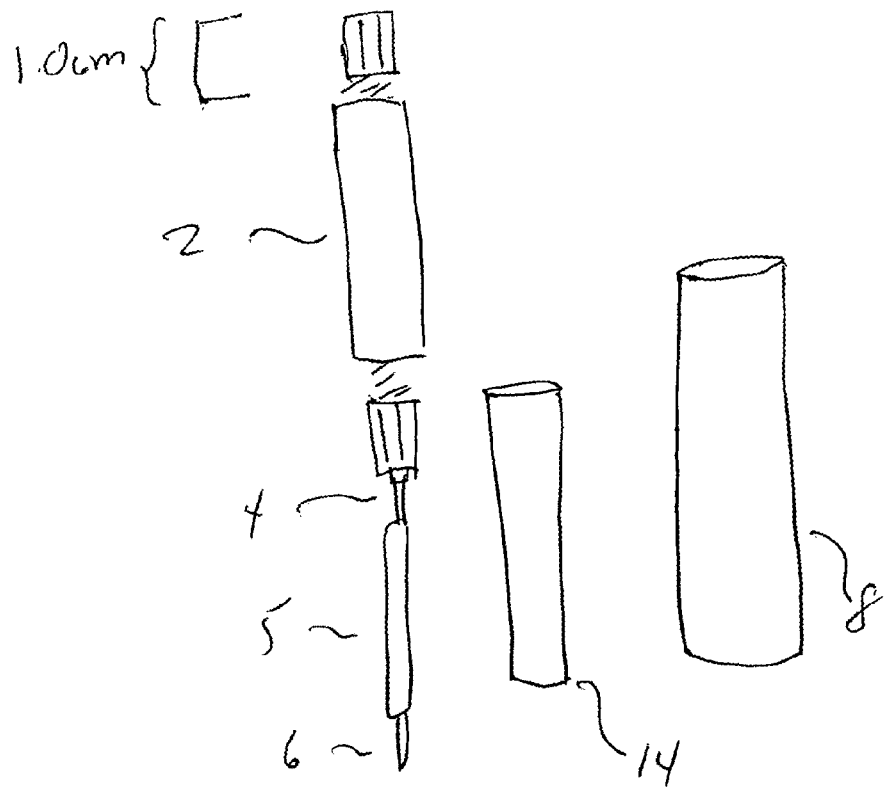
Figure 10 Inductor Parts.

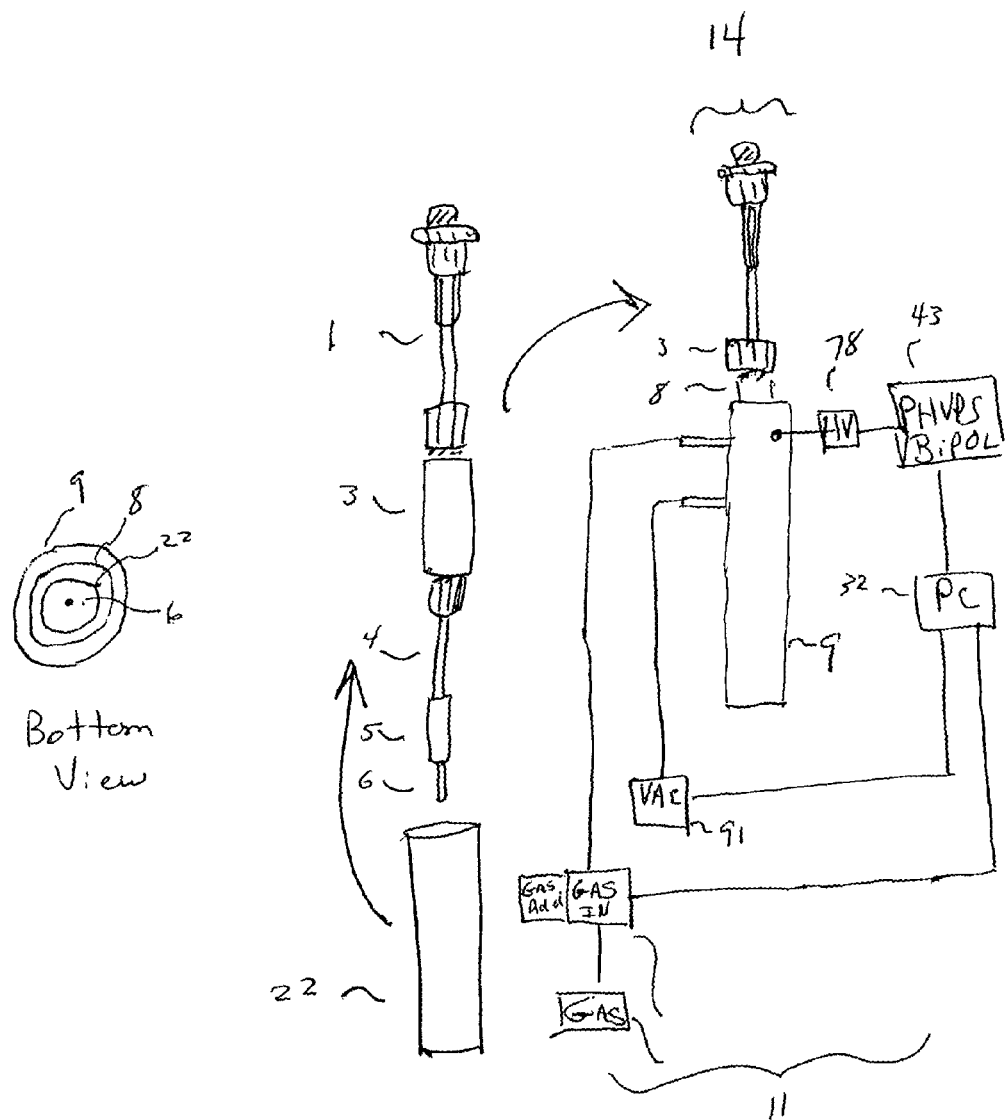
Figure 11. Inductor version 2.0 with internal parts and with gas in/out and with in this case a digital programmable HV power supply.

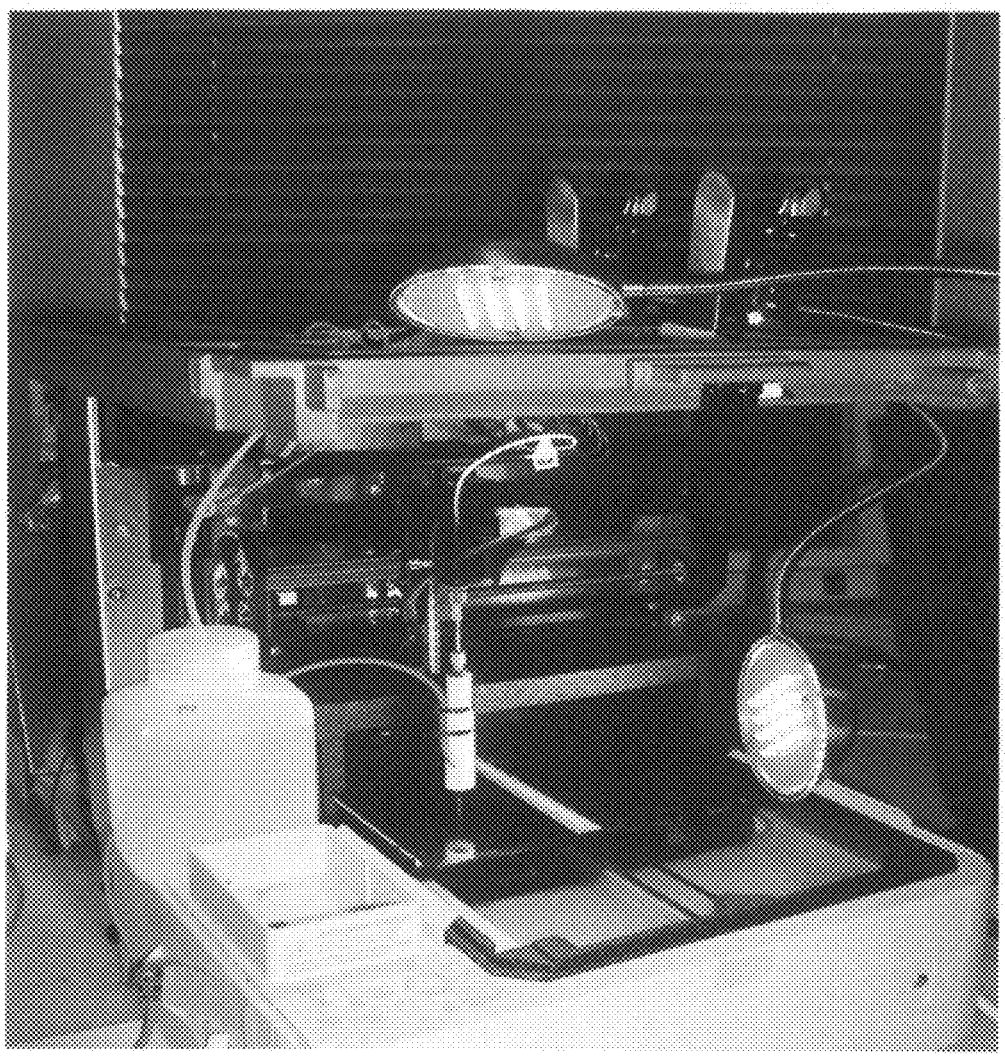
Figure 12. Spark Holland Alias with installed inductor above 384 stainless steel MALDI plate.

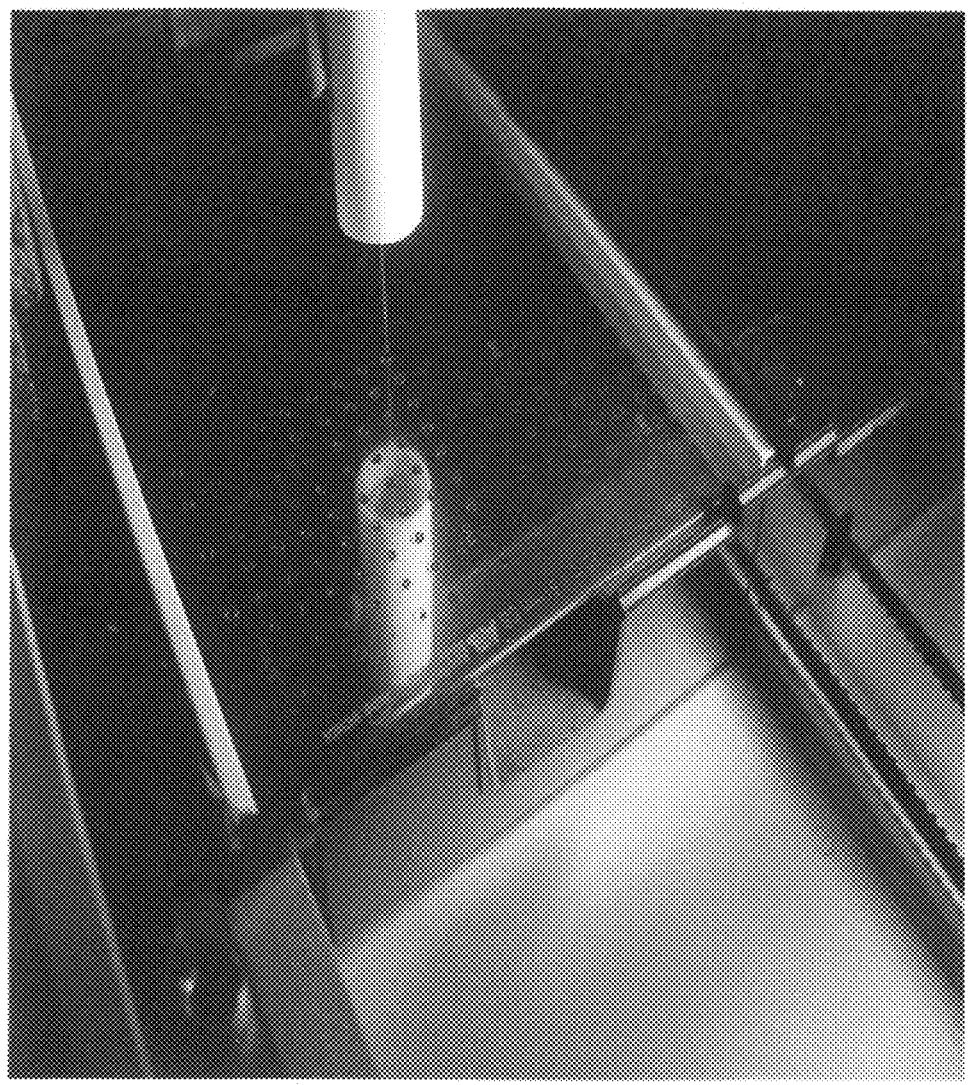
Figure 13 Nanoliters placed by IBF on a MALDI plate.

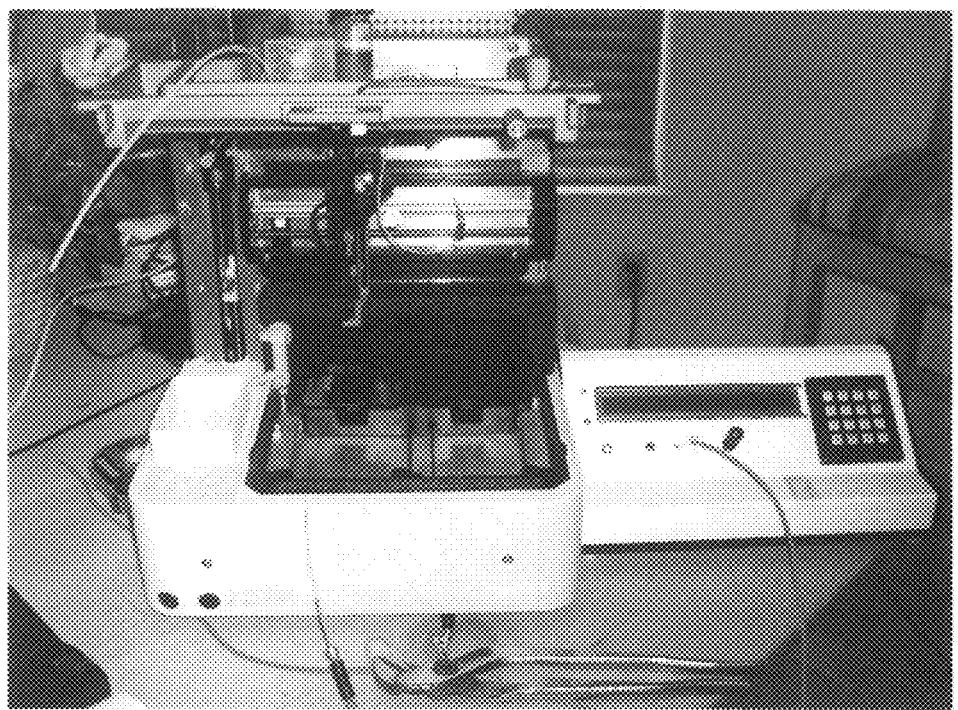
Figure 14 Nanoliter digital wave version 1.0 with Spark Holland Alias.

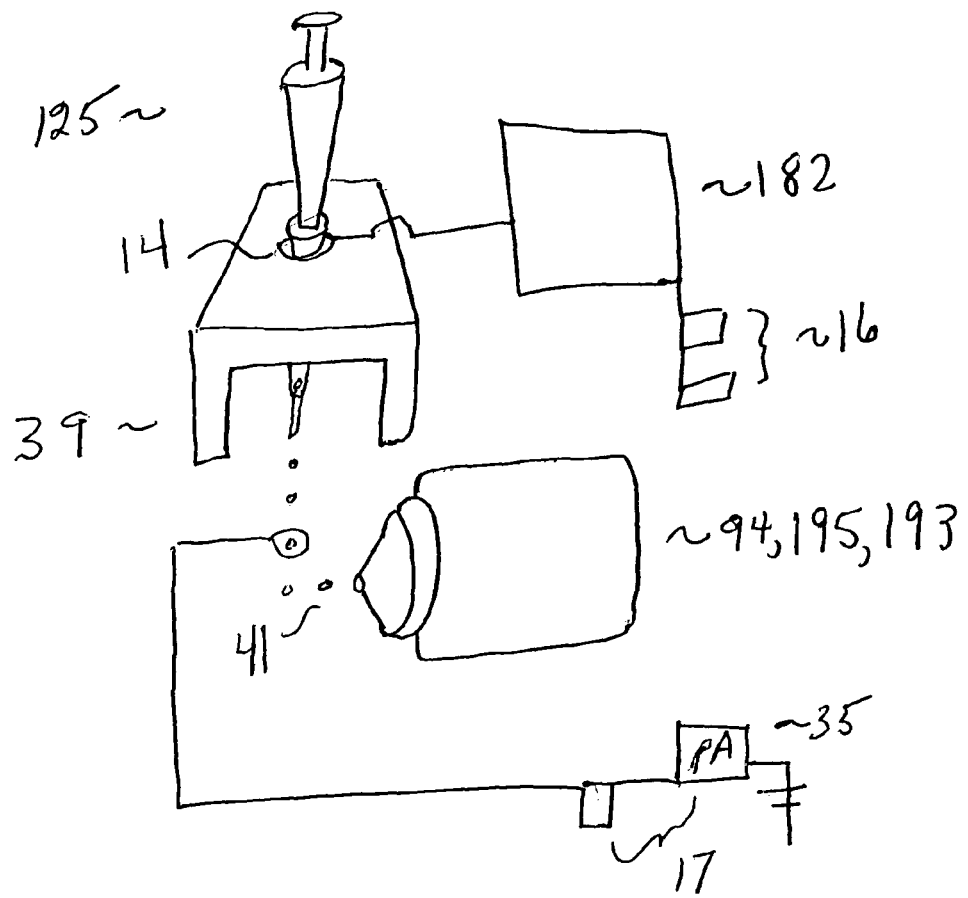
Fig. 15 Pipette, G2 Gilson MS via IBF

Fig. 16A
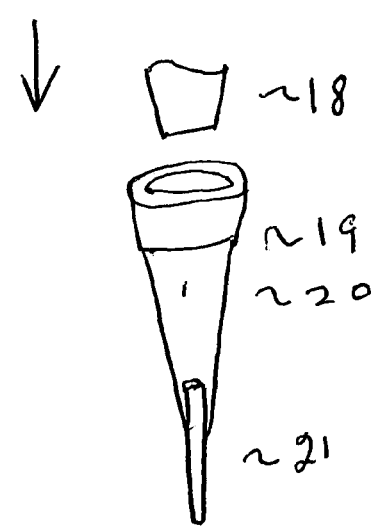
Fig. 16B
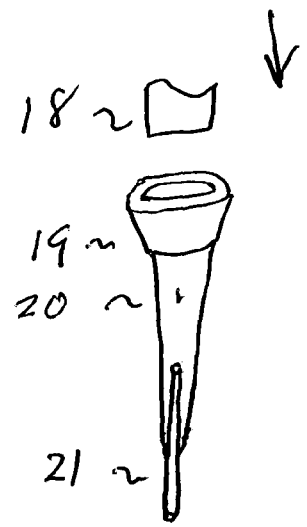
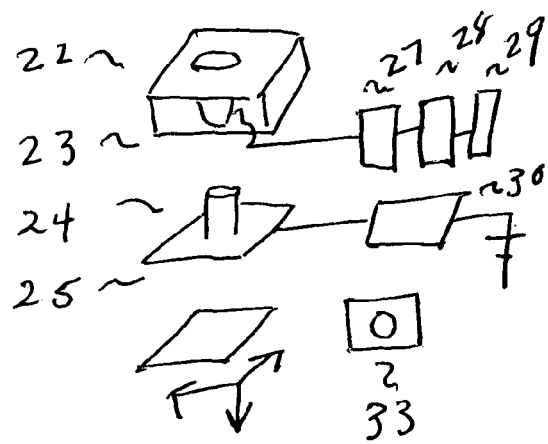
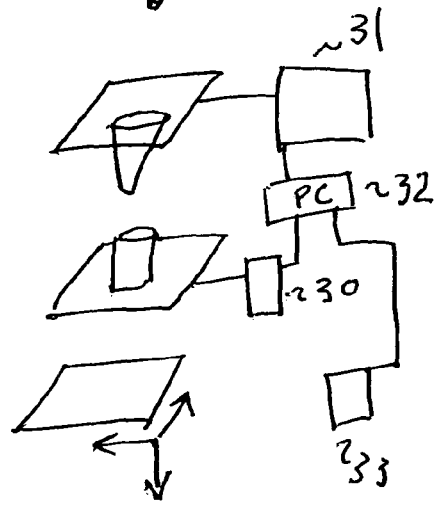
Fig. 16 Analogue + Digital nL pipette tips

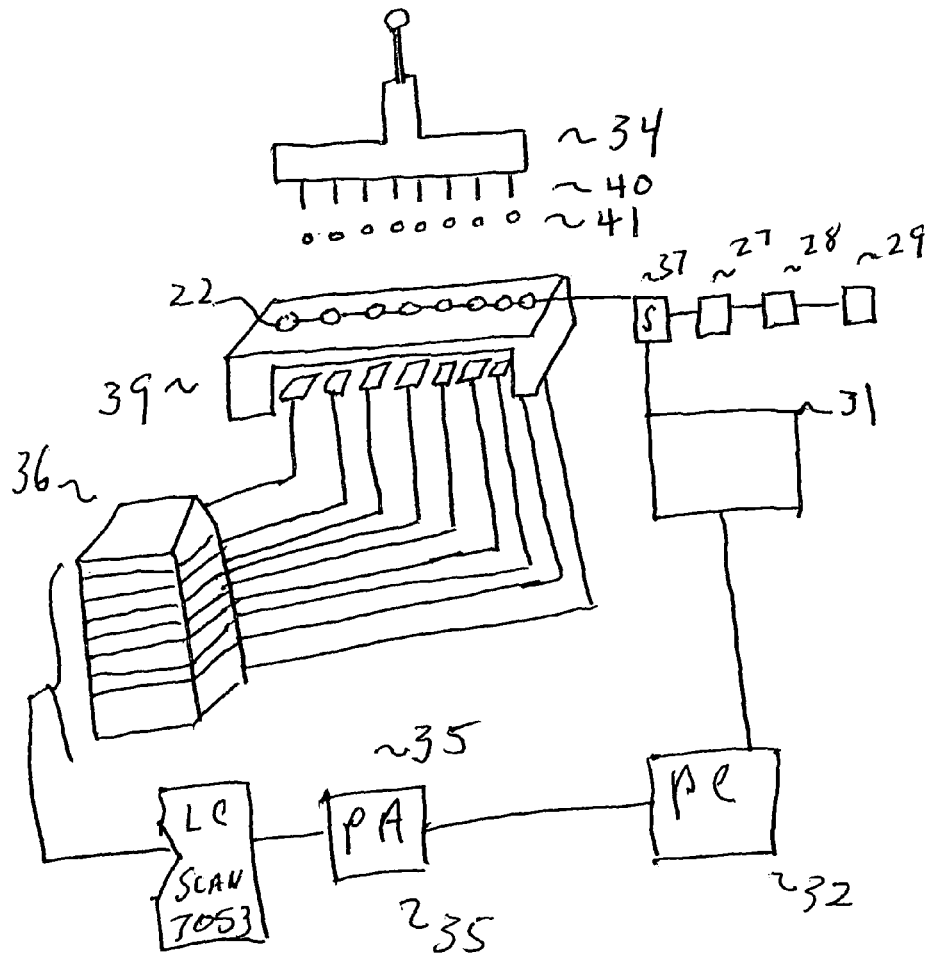
Fig. 17 A/D IBF Pipette

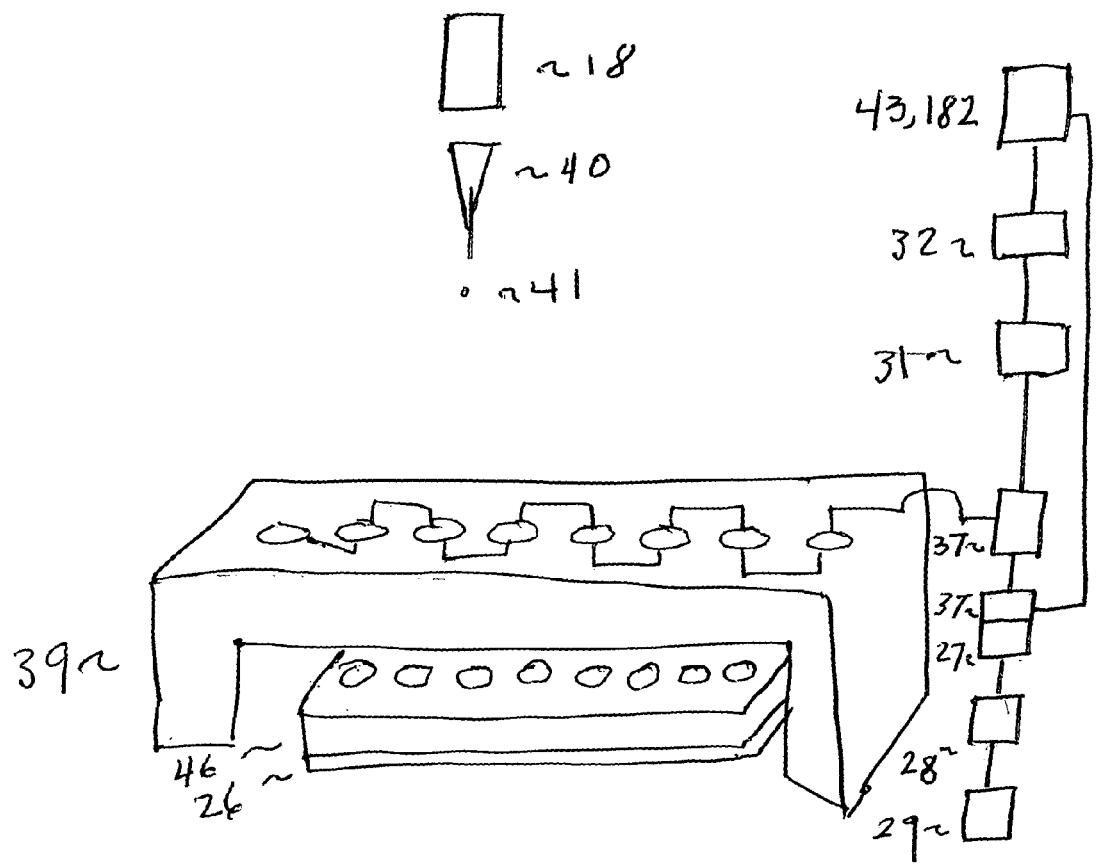
Fig. 18  A/D IBF Pipette

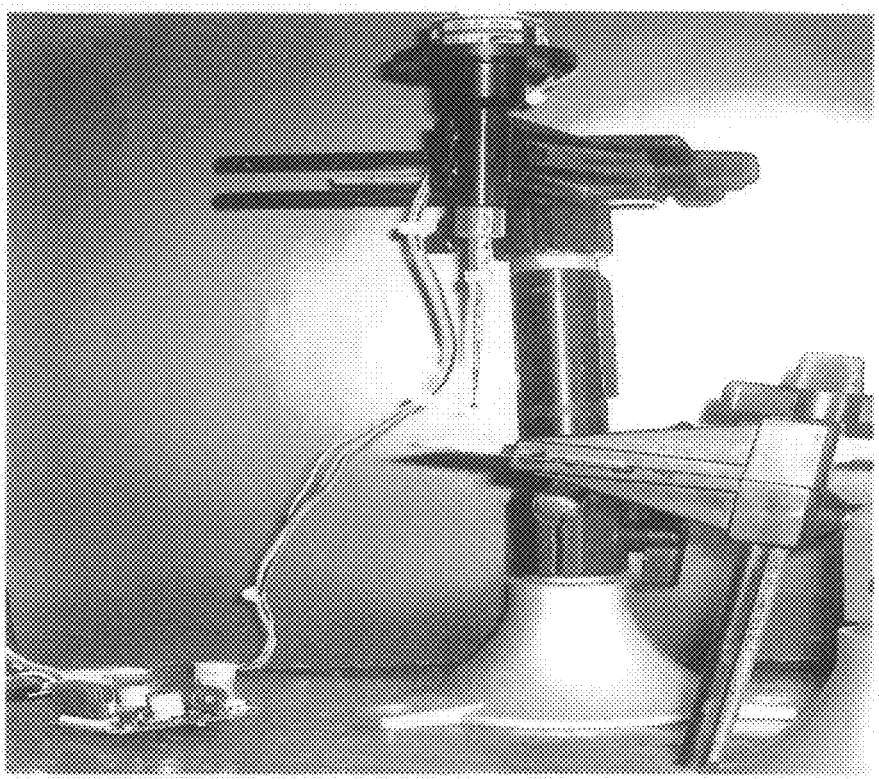
Figure 19 Nanoliter air displacement pipette

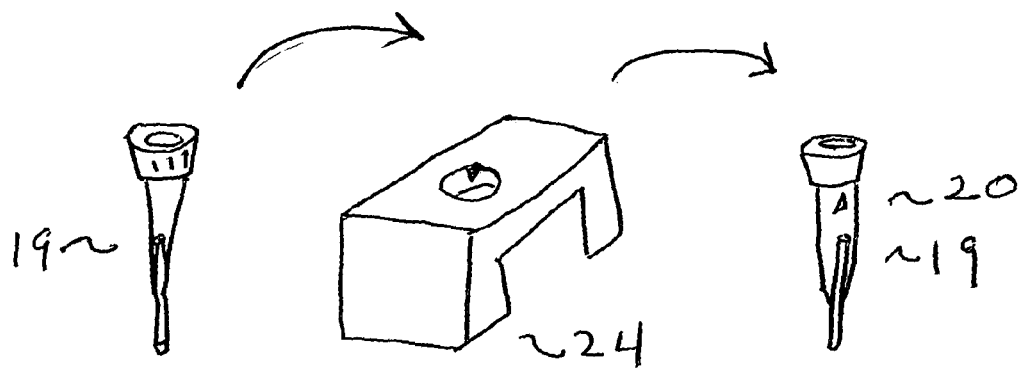
nL pipette tip + whole
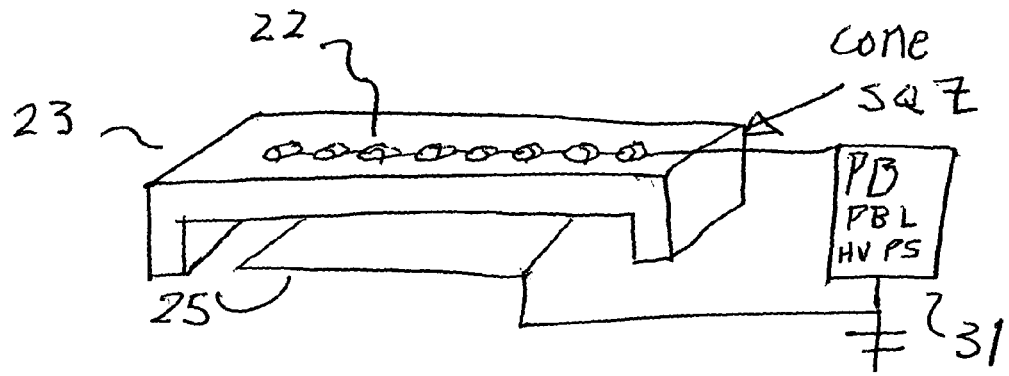
Fig. 20 nL pipette devices

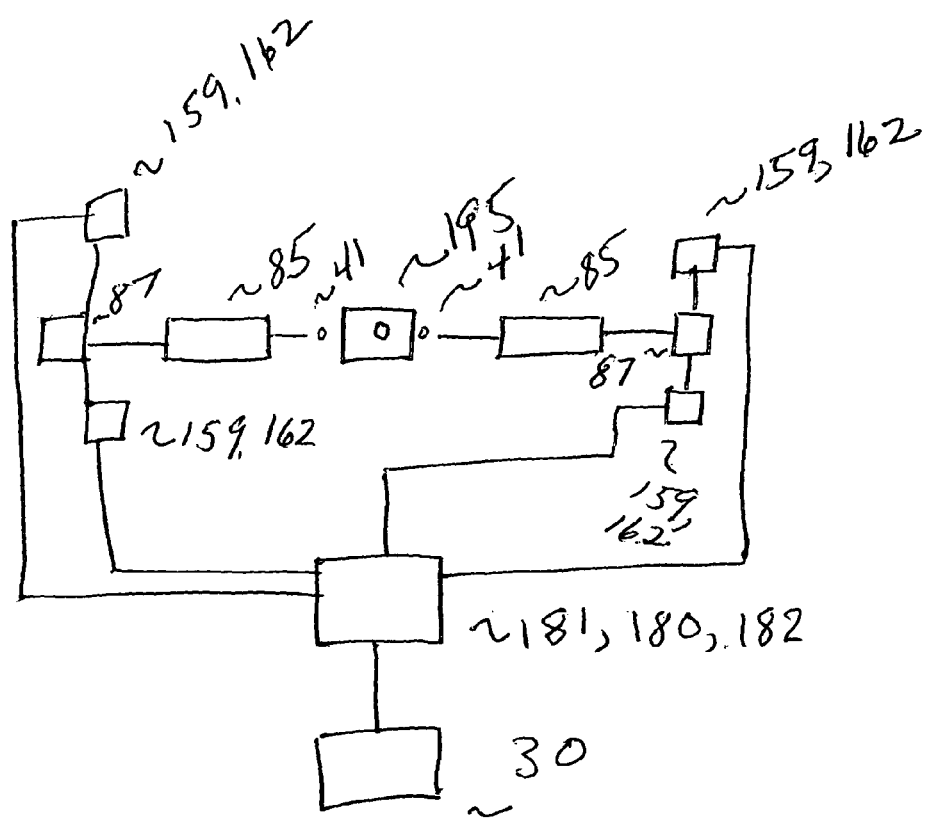
Fig. 21 parallel UPLC

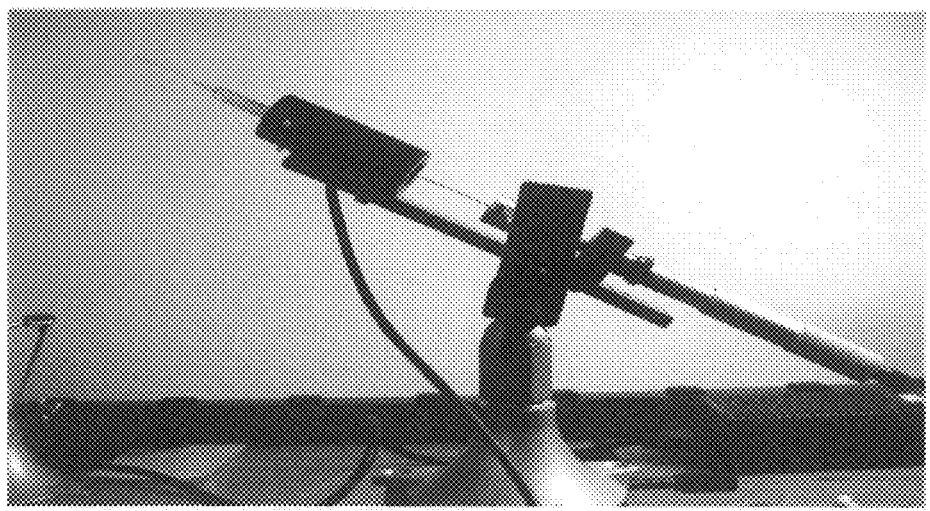
Figure 22 Nanoliter syringe showing holder, micrometer, coupler, 10 uL metal syringe that has been cut, quartz GC union, fused silica tip.

nanoliter Cool Wave® Syringe

Fig. 24  Syringe w/ E Focus

+/- Switchable
Charged polymer device

Fig. 26 Switchable: Polarity, Energy

Fig. 27    IBF Induction Device

Fig. 28 n channel ultra high pressure sample preparation.

Fig. 29 Spark Holland
Alias, FBF

Portable IBF Spotter a supply  b micrometer  c inductor
d base    e wire         f hv wire  g holder
h syringe  j coupler

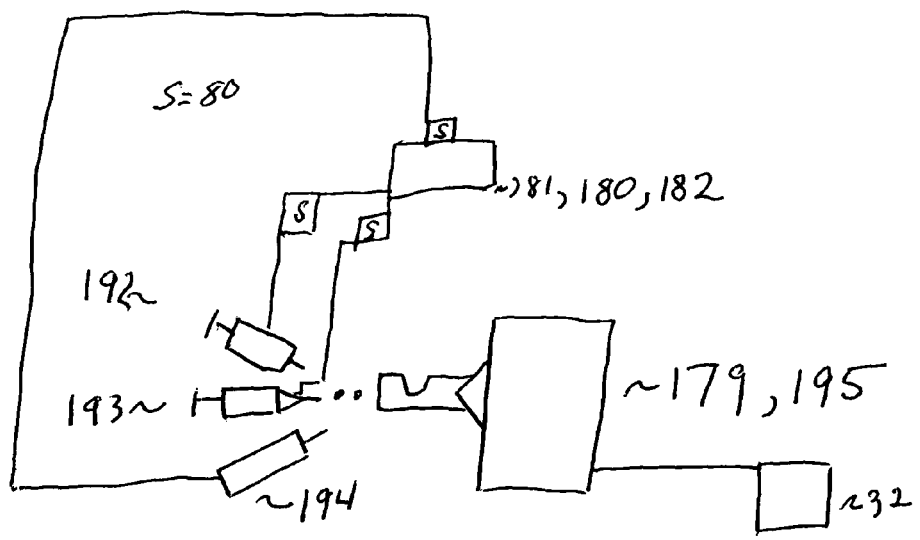
Fig. 31 Syringe, Pipette & Pump MS

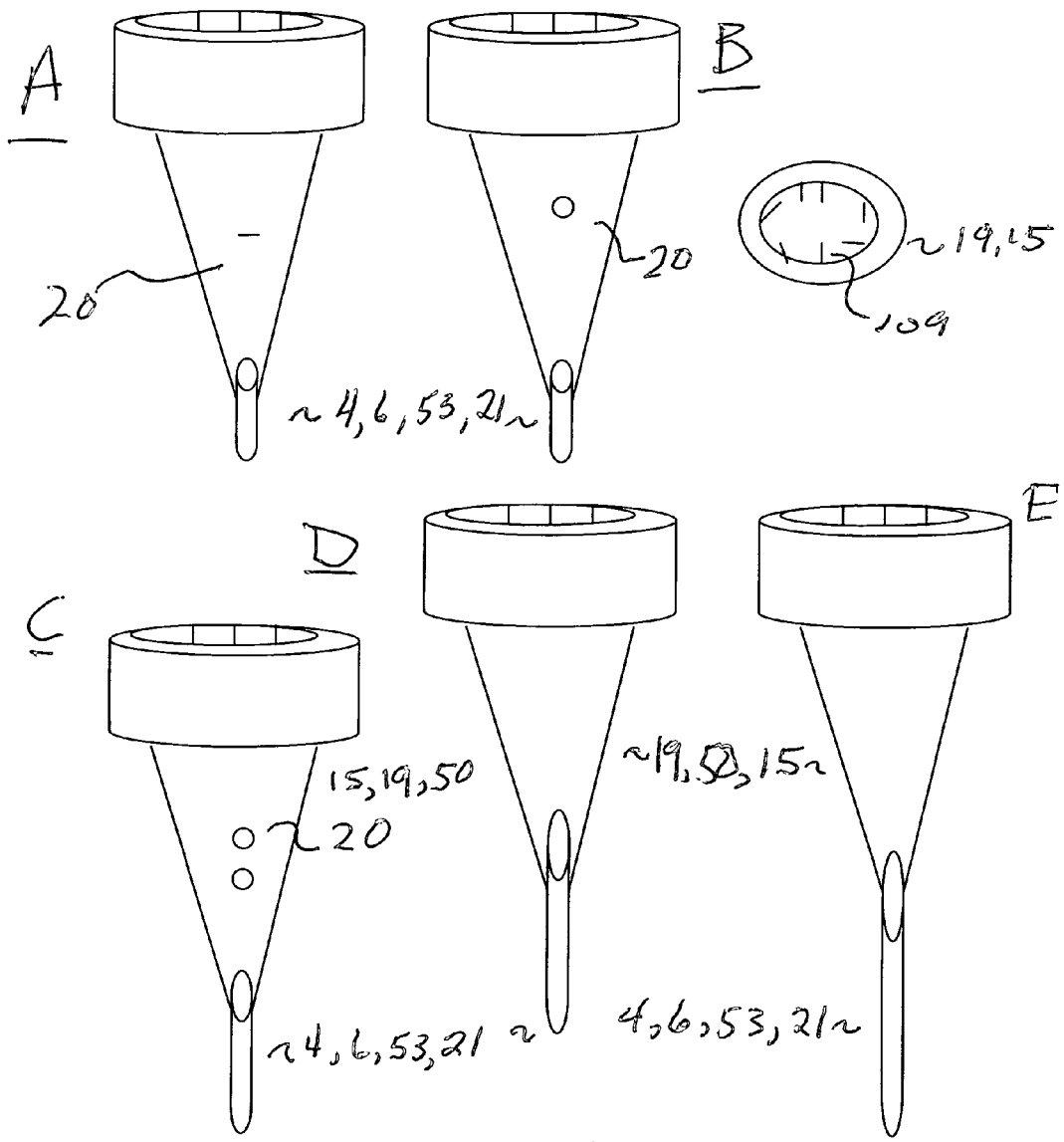

Figure 32 Compression fit Teflon, perfluoromer, nonpolar fused silica, quartz and other coated capillary into pipette tip with optional tags that allow for tip to hold to pipette or device without air tight fitting so capillary can fill. Different capillary radii and length yield different volume for same or different device. Interior of capillary optionally deactivated with chemicals like trimethylchlorosilane and heat.

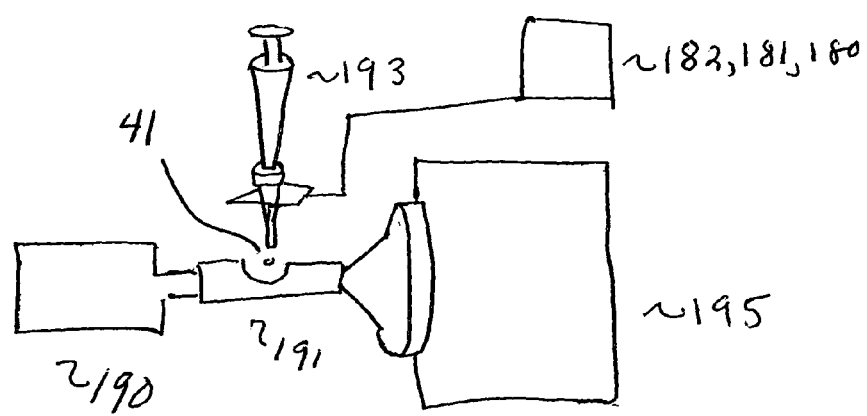
Fig. 33 nL into MS

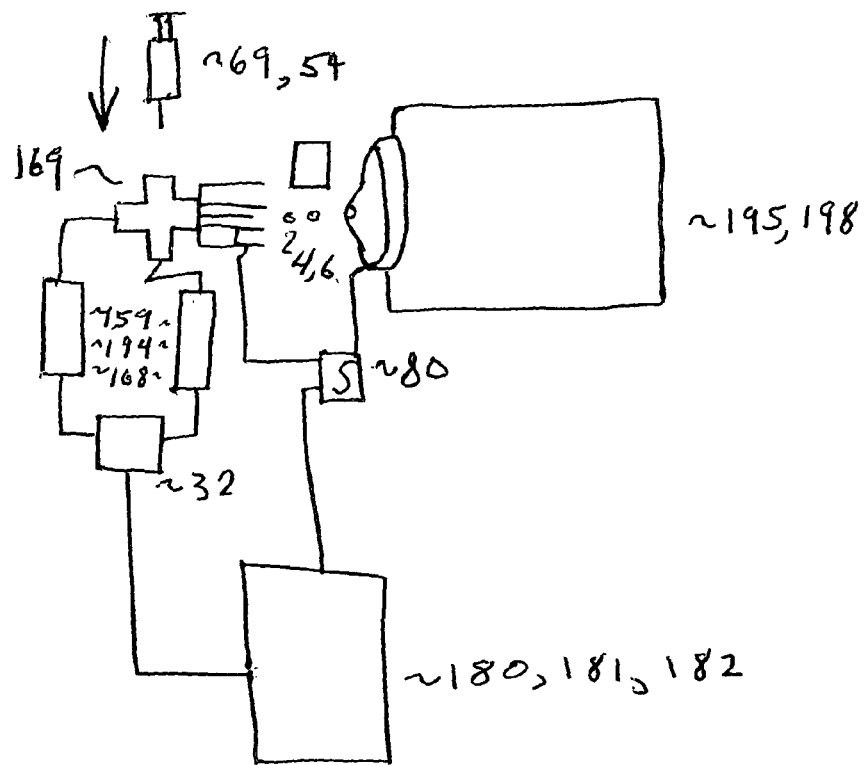
Fig. 34 nL pump + mass spec

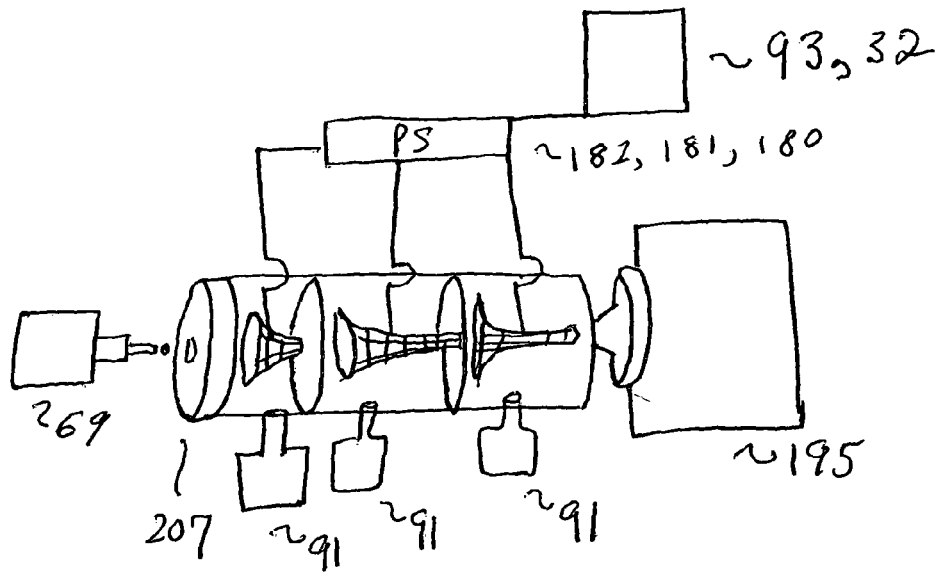
Fig 35. Neutral Pump Away

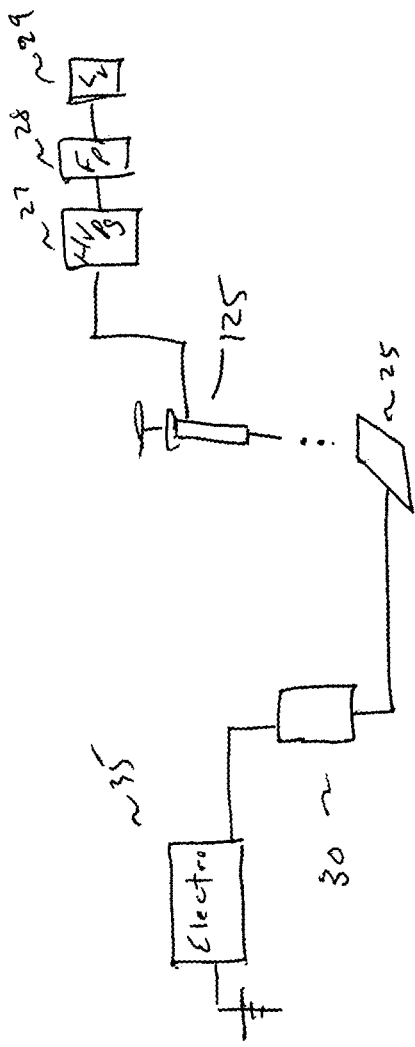
Figure 36 Low Current Liquid Measurement Device

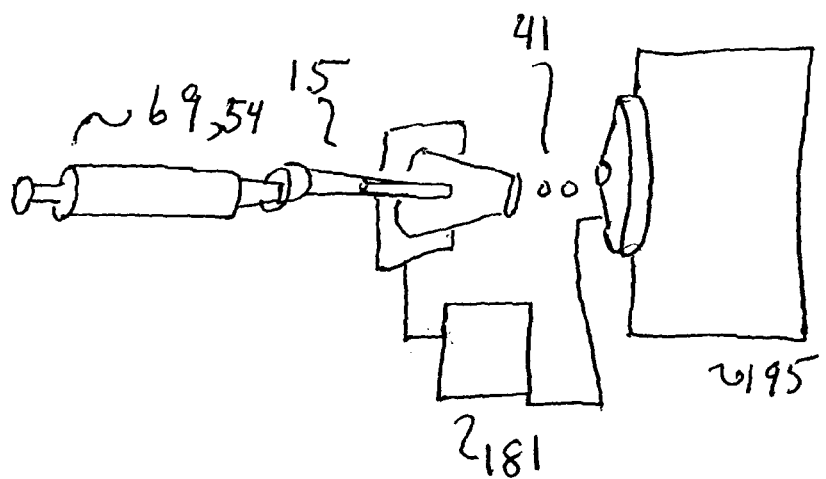
Fig. 37 Multiplexed MS

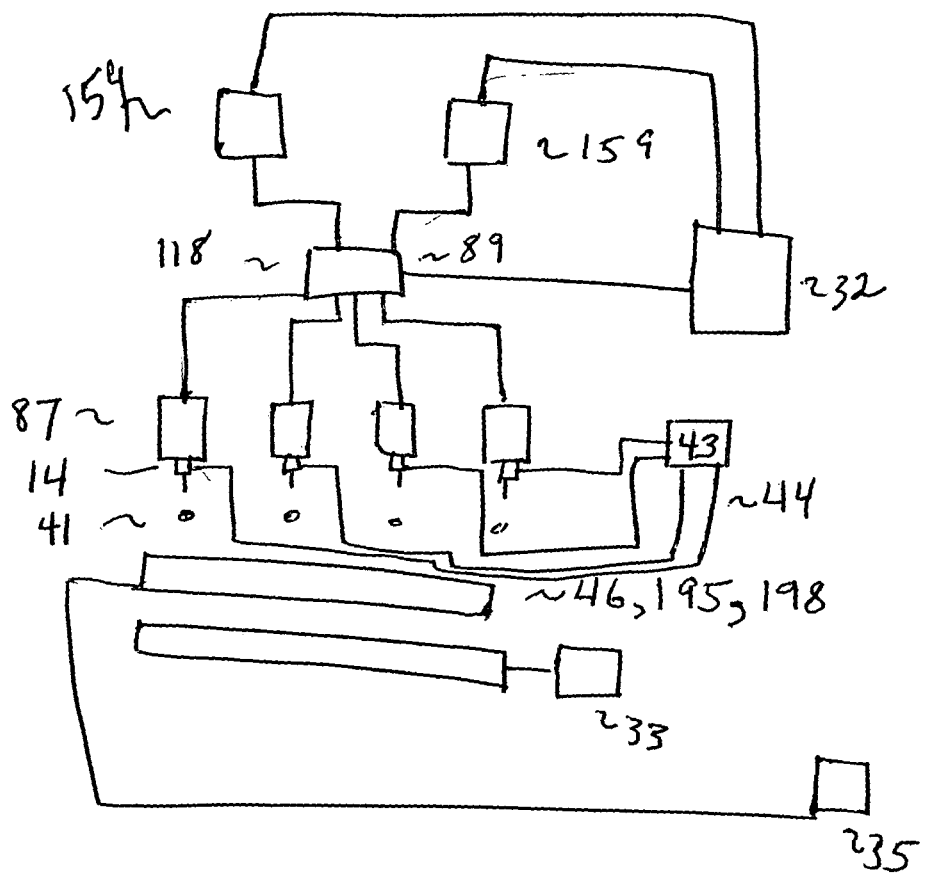
Fig. 38 Four Channel LC/MALDI

IBF BASED LCMS

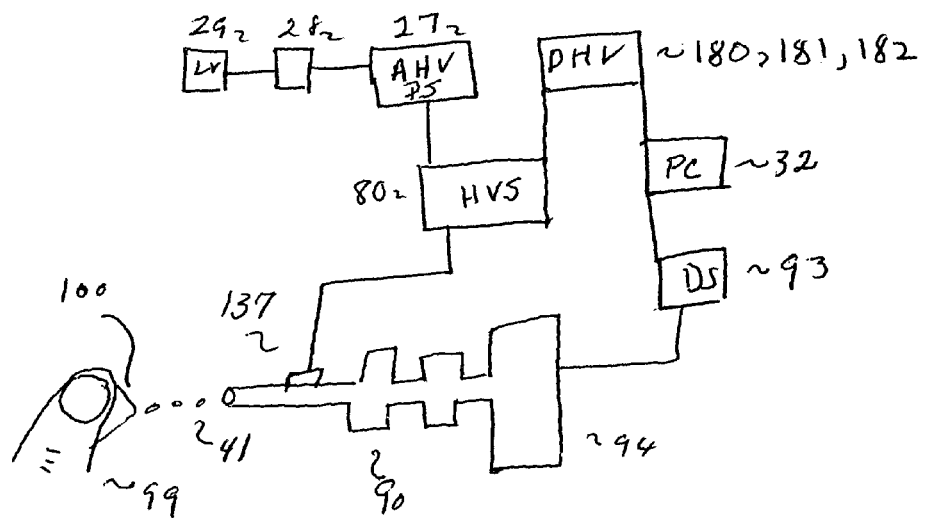
Figure 40 Human Sampling Device

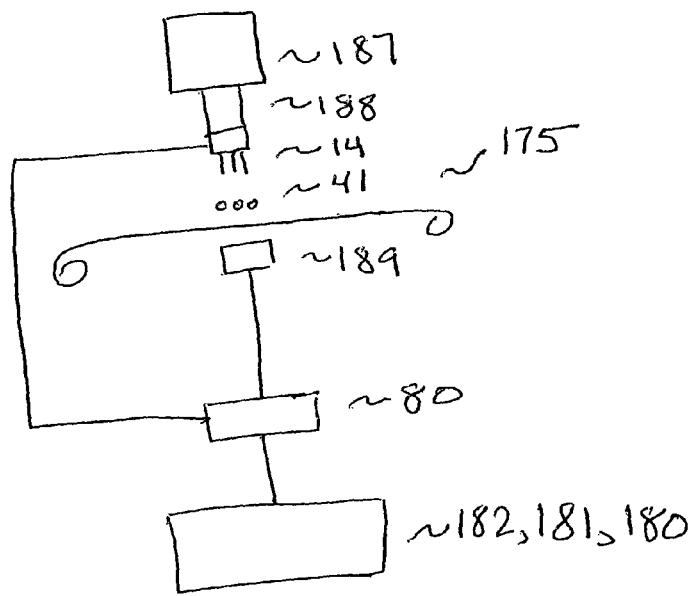
Figure 41 N Channel Programmable Dispenser Onto Plastic or Tape

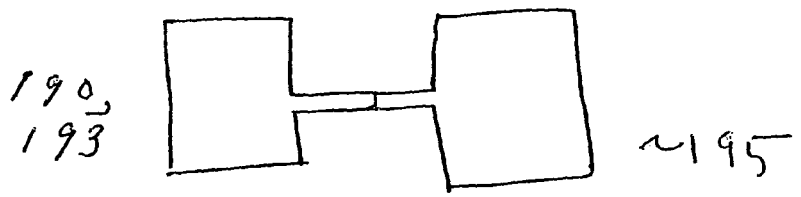
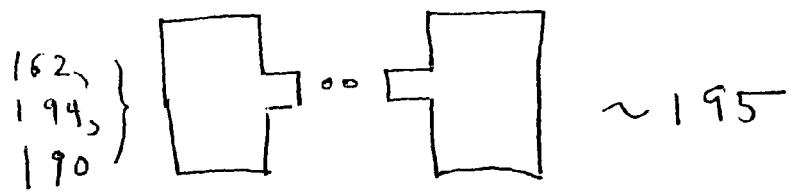
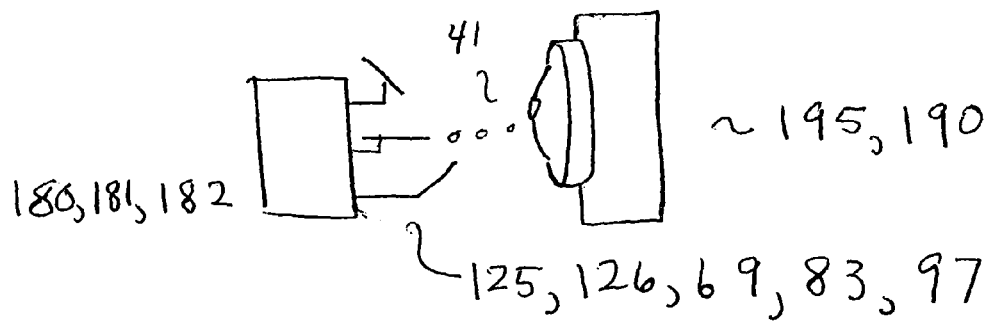
Fig. 42  MS with IBF AND Declustering Unit

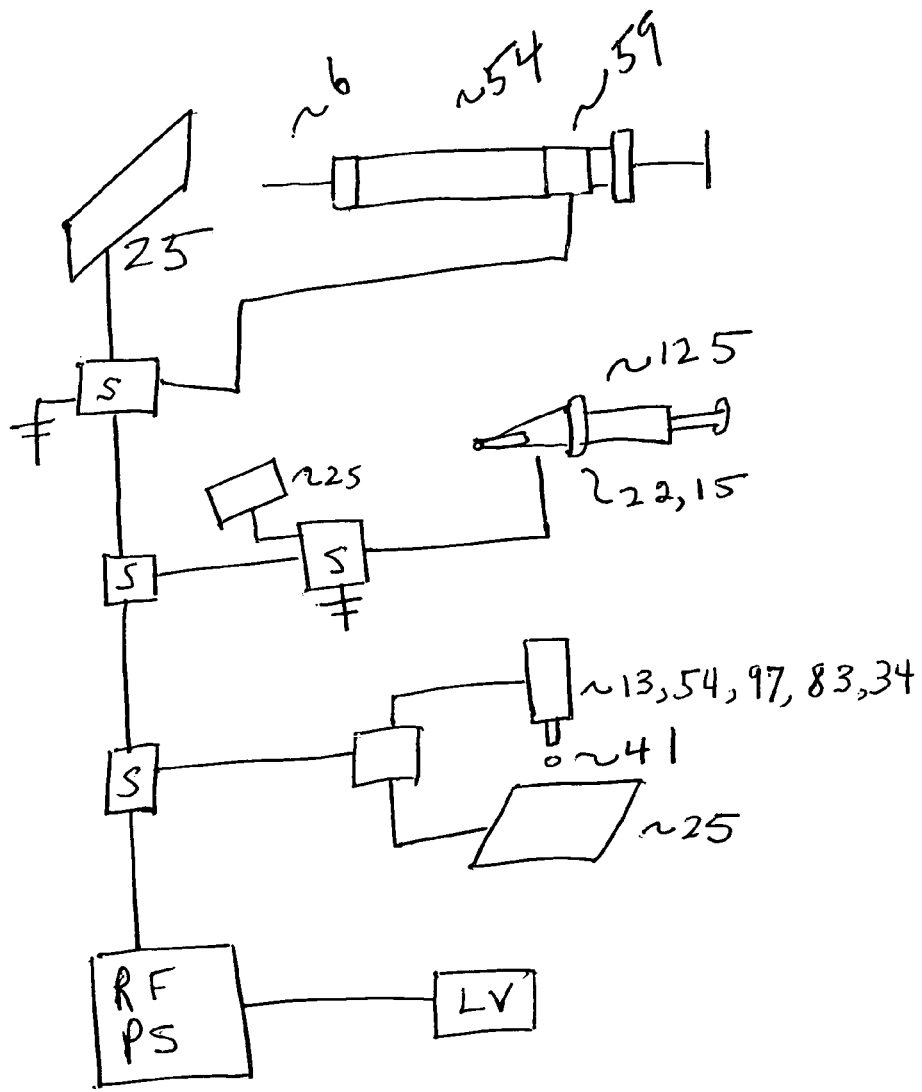
Fig. 43 RF Dispensers

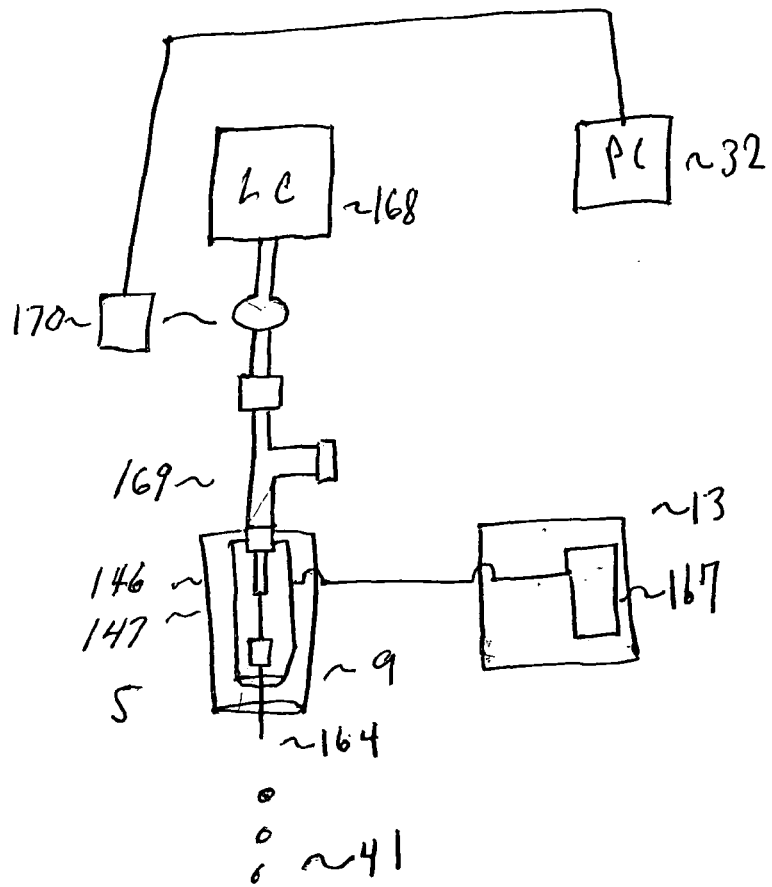
Fig. 44 µℓ IBF System with ZDE union.

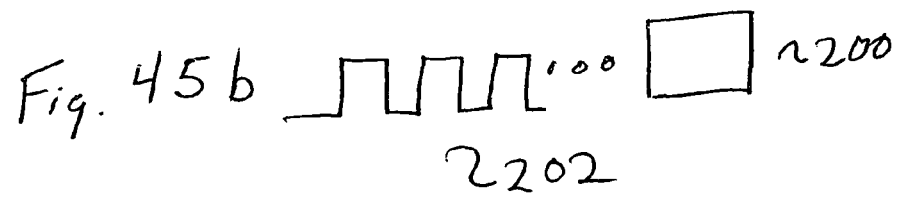
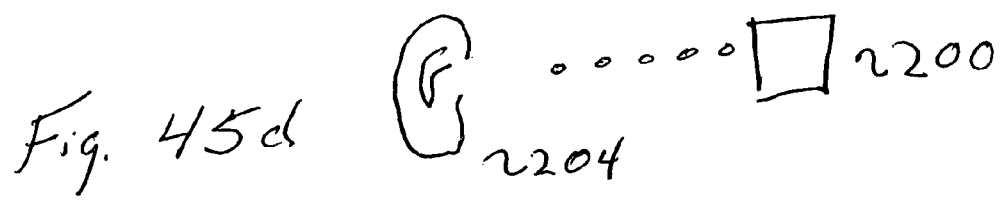
Fig. 45 nL dispenses on to humans + human parts

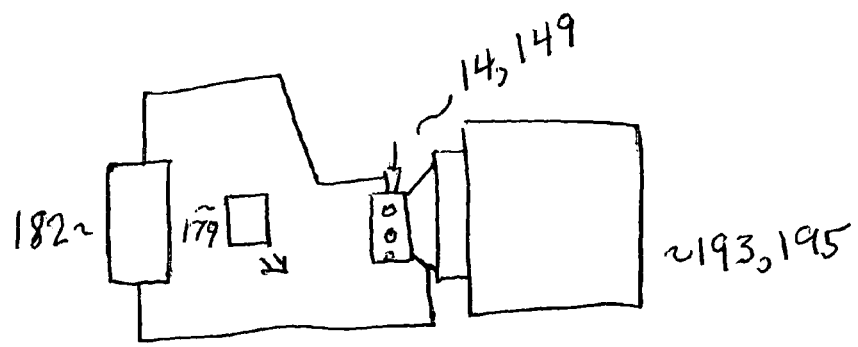
Fig. 46 N channel UNION

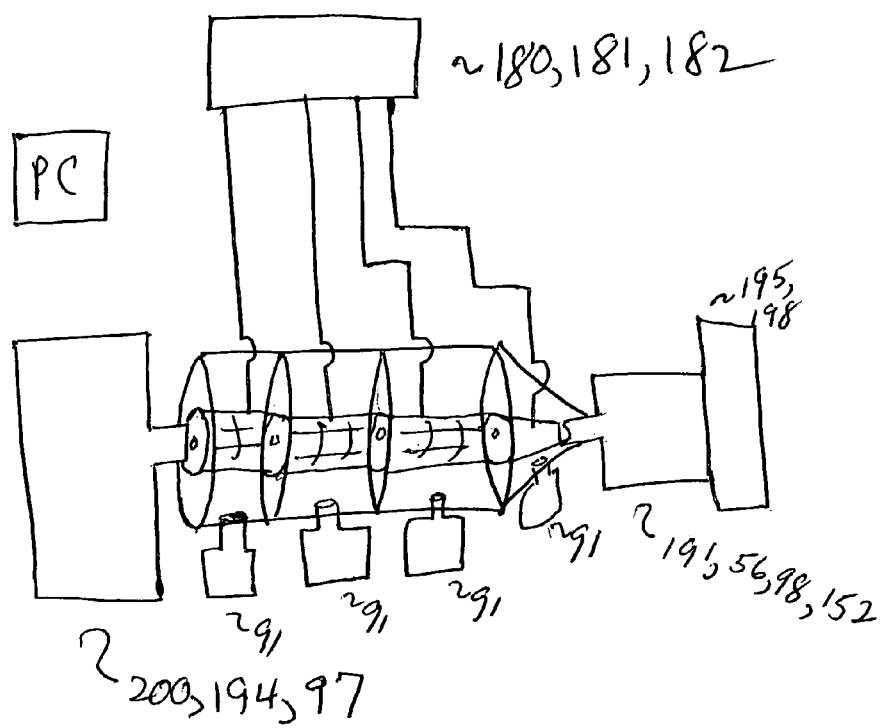
Fig. 47 Accelerating Denuder

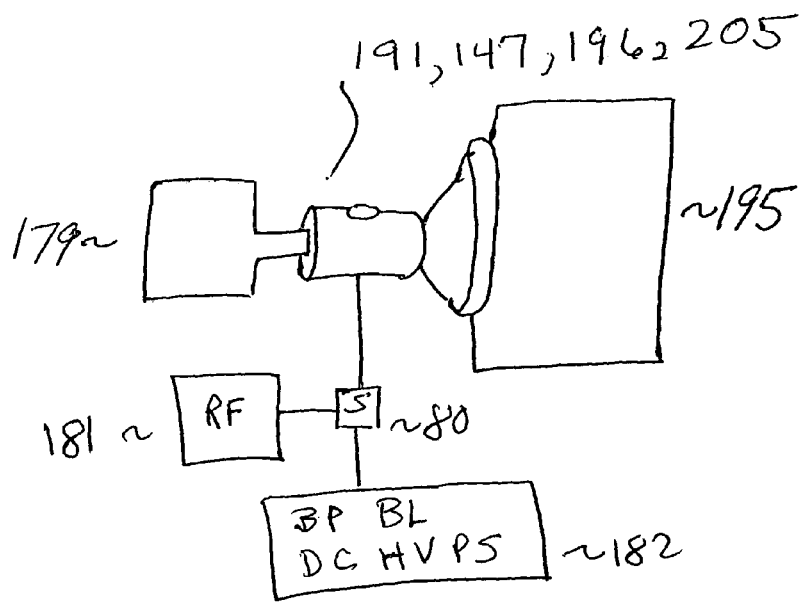
Fig. 48 MS, DART other Sample Introduction Tool

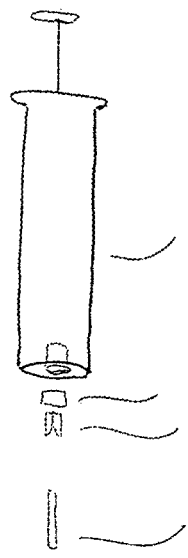
Figure 49 Compression fit, easy change Syringe Tip System Syringe + Tip System

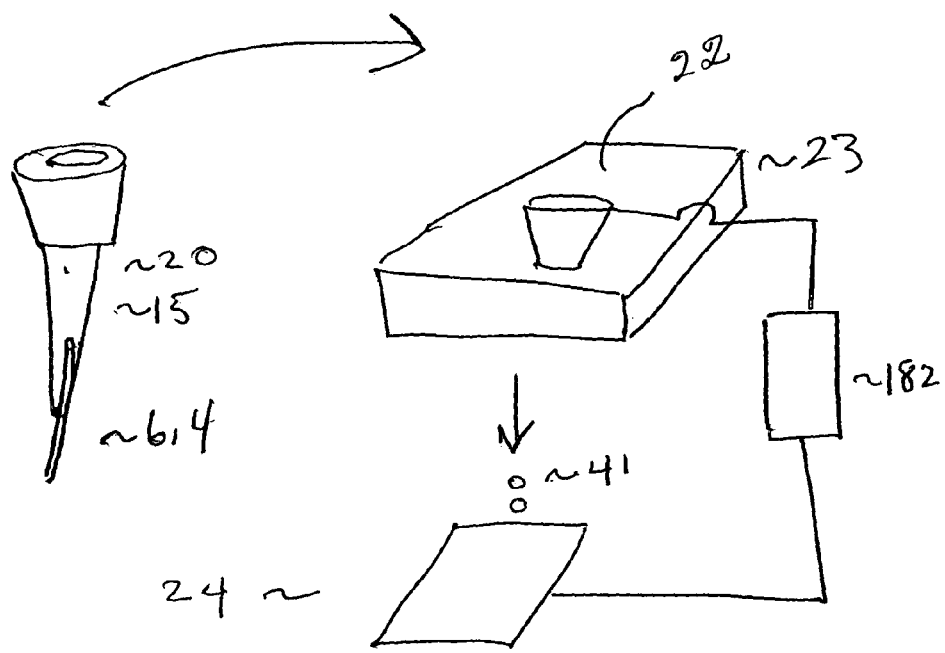
Fig. 50 nL pippette tip

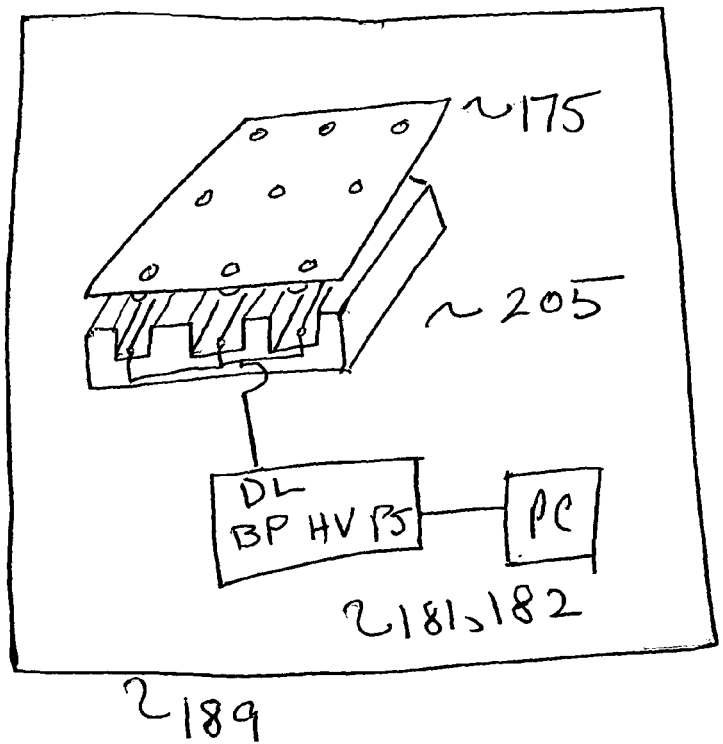
Fig. 51 DL Bipolar HV Power Supply + Array Tape Inductor

Fig. 52 Dispensers + Tips

INDUCTION BASED FLUIDIC (IBF) AND HYBRID DEVICES FOR THE MOVEMENT, TREATMENT, MEASUREMENT, INTRODUCTION AND MANUFACTURING OF LIQUID/S AND OTHER MATTER

This patent application claims the filing date of Appl. No. 60/881,532 which is Jan. 22, 2007.

BACKGROUND

Accurate and precise liquid, solid, and matter movement or transport of dispensing across the macro, micro and nano worlds to a destination is of interest in countless areas including: drug and liquid product manufacturing; proteomics; genomics; bio and other agent detection; forensics; homeland and airport security; medical diagnostics and other health care area; environmental and other areas and manufacturing of all types. The ability to accurately and precisely transport liquids can be employed to manufacture drugs or prescriptions; prepare samples for chemical analysis or for medical diagnostics tests by many techniques, for bioagent detection and the standardization of such measurement processes or for handling such materials or for forensics testing; to place chemicals, drugs or samples onto food, plants, animals humans (or take them off) other objects or into scientific or other instruments or to perform isolation and purification functions; such as, filtration; solid phase extraction (SPE) and liquid chromatography (LC) in one or a plurality of channels using only IBF or so doing with hybrid, coordinated and programmed multi energy source. The ability to manipulate small and large quantities of liquids using electric fields has other lesser known potential including: manufacturing new entities such as electronic components; frozen charged functionalized chemical entities and polymers that we have called nanoliter-sicles or more recently chargemers, in cooling applications, in repairing crystalline optics for large lasers, for parallel liquid chromatography, solid phased extraction (SPE), filtration and increasing the dynamic range of solution transport to existing pumping systems of diverse types.

Devices that transport and optionally simultaneously treat and measure low quantities of liquids for such purposes have historically been largely mechanical in nature and they include: microliter syringes of all types; capillaries with attached bulbs; single and multichannel pipettes and many different types of common pumps. More recently other devices have been applied to transport small quantities of liquids for various purposes including: piezoelectric devices; ink jets and other electromechanical devices and lab chips. Such devices are not capable of dispensing liquids and performing useful functions across the macro, micro and the nano regimes (i.e., from mLs, to uLs to nLs to pLs to fLs) singly or in parallel with one source of energy or with multiple sources of energy whose programmed application is coordinated or integrated and that can measure and verify liquid movement and treatment launching and directing the product to targets. Either they cannot accurately transport the liquids across such a dynamic range or they have adverse properties including: inability to overcome adhesion and/or cohesion of small volume of liquids or liquid drops adhering to surfaces and as such they must touch off the liquid possibly contaminating the liquid or target, the device or both. Or once launched, they are not directed to the target or counted on arrival across the micron to meter distances used in labs and factories. Alternatively, even when for example low volumes of liquids are produced (but not higher volumes) they are not directed by the drop producing process and they can take trajectories that are not directed to locales causing errant location dispensing. Also, many low volume dispensing systems have large dead volumes, are complicated, and expensive in design and requiring at least one energy source per channel. Also they can exhibit adverse electrochemistry; produce joule heating; or combinations thereof; that impact reliability and cost. Also, such devices again, cannot create and energize liquids, creating either drops or sprays, launch (i.e., via a push or pull force, as when either the device or target is charged) such that they are actively directed to locales or targets that can be non-conducting or conducting doing so without touching the target as it provides the energy to overcome the adhesion and cohesion of a liquid or liquids in drop, spray or hybrid form on the nested gaussian surfaces, N channels at a time with a minimum of one source of energy or optionally more than one source of energy that are integrated to an affect with IBF, as they optionally measure the amount of matter transferred.

Technology that we have called induction based fluidics can make a simple capillaries, common syringes, pipettes, pumps of all types dispense, treat, introduce or optionally modify polymeric liquids over more than nine order of magnitude and it has massive application space in matrix assisted laser desorption ionization mass spectroscopy (e.g., LC/MALDI) in cancer diagnostics and proteomics, for sampling humans in a non dispersive manner, for placing drugs onto humans, in polymer characterizations and polymer manufacturing, in the area of cooling entities in enclosures and many other areas of health care and basic research and in manufacturing of drugs and special entities.

We have patented (U.S. Pat. No. 6,149,815) and have now three pending patents and technology that can dispense liquids as it also performs functions across a massive dynamic range of literally in certain configurations and energy from mLs to fLs whose core process has no moving parts, no joule heating, no adverse electrochemistry (i.e., faradaic processes) and that can perform parallel dispensing, parallel solid phase extraction, parallel filtration, parallel LC and parallel instrument introduction and more using as few as one source of energy and often very powerfully integrated IBF-other energy forms or types where for N channels where N can literally be a very large number, as it directs the liquid to targets.

We have taken this patented tool set that we call induction based fluidics and we have expanded the capabilities to small, less complicated even handheld devices that can dispense, literally fly liquids, as it directs liquids in the uL, nL and pL volume range using off-the-shelf devices like microliter syringes, pipette tips, pumps of all types developing a totally new technology that can place nanoliters onto humans or take them off of humans or make MALDI spot plates in parallel or manufacture charged frozen nanoliter spheres that we have called nanoliter-sicles and that an be made into charged polymers, chargemers, that can be aspirated by charged on non-charged rods, and as we have merged this IBF technology into more traditional older pumps; so that, IBF can be applied in tandem to other liquid transport technology gaining the benefit or IBF including a wide dynamic range, highly parallel dispensing and other sample treatment options, excellent volumetric and spatial accuracy and precision plus unique capabilities and significant advances to larger fields of application. In addition, we have now added new technology that an simplify these task using new circuitry, disposable tips, current measuring devices, in mounted, robotically assisted or in handheld embodiments of using inductive or conductive energy transfer tools that can be either battery operated or DC or AC powered. Powerfully, this new integrated IBF system can be adapted to virtually with any current robotic based or other dispensing system at low cost, as we have done with devices as diverse as a Gilson, P2 pipette, a Hamilton 701 microliter syringe, or Spark Holland's Alias LC liquid handling robotic system.

In summary, this application extends IBF such that the technology can employ as little as one source of electrical energy alone or use multiple sources of energy in an integrated manner or where multiple sources of energy are coordinated in tandem to transport, launch or fly, move or dispense rapidly one or more liquids as a low volume discrete aligned drops or spray to non-conducting or optionally to conducting targets one at a time or in a highly parallel manner across the mL, uL, nL, p L and fL dynamic volume range as it actively/passively directs the liquid to precise locations on inanimate or animate targets whether they are conductors or nonconductors. When the nested, gaussian surfaces so energized contain filters or fits, SPE media, chromatographic phases, immunoassay or other functionalized media the device can perform many functions in a highly parallel manner on the liquids; such as, filter, extract, chromatograph, purify and place or otherwise transform the liquid and other matter or its contents as they serially perform the transport function in a parallel mode optionally placing the liquid onto a target or targets be they surfaces, containers, scientific instruments, chemicals, drugs, food products, plant, animal or human subjects or other targets as it provides one or more ways to quantify the volume, and locations of the liquid/s providing other ways to facilitate operation. When the current of such process are measured by electrical, visual or thermal means, one channel or multiple channels at a time and written to digital media the transport of matter or composite actions can be verified and recorded.

When such systems dispense monomers, they can produce upon polymerization unique polymers called chargemers or in other applications when the use of inductive surfaces are energized, cooling effects can be produced in enclosures cooling the contents thereof and finally because of the ability to launch small drops directly and to keep them aligned by electric fields this technology can be used to shoot liquids into mass spectrometers (MS) and other scientific and other instruments increasing greatly, the sensitivity of all types of technology; such as, electrospray ionization (ESI) MS.

This application further extends IBF and previous work, through the application of unique energy inductors that can be appended to existing devices and whose energy can be programmed in one or more form to effect liquid movement into microtiter plates or onto MALDI or other surfaces Because the physical movement of fluids; solids; slurries; drugs; solvents; and charged matter is so elementary to so many processes in biotechnology, health care, manufacturing, daily life and other areas it is impossible to adequately address all applications of this matter transport technology.

SUMMARY OF THE INVENTION

Apparatus employs electric induction to transport liquid and other matter for multiple effects using extremely simple to complex systems. The apparatus employs a unique electrokinetic inductor/s and circuitry in conjunction with optional manual or programmed energy sources and sampling devices, computer integrated hybrid source/s of energy that use electrical and other programmed or manual energy sources, transports with active/passive liquid direction to the target that can also treat, count, and introduce or abstract liquids and other matter as it monitors liquids, slurries and other matter including some solids launching them to locales or targets through or using Gaussian surfaces or nested Gaussian or other matter surfaces independently or optionally in a hybrid mode using inductors (energized formed surfaces and directing surface) with electrical HV or low voltage DC, DC/RF or RF electrokinetic whose application is applied inductively or in an inductively/conductively and that is integrated, co-ordinate and programmed to effect energy transfer from simple devices like pipettes, capillaries, manifolds, syringes; plungers; siphons; and other matter, but that can energize in an optional hybrid mode with more complex devices; such as, syringe pumps; pneumatic pumps, air displacement pumps, piezoelectric pumps, sound devices; peristaltic pumps, ultrasonic pumps, thermal energy, liquid chromatographs (LCs), or electrokinetic movement devices (e.g., Lab chips, capillary electrophoretic systems or LC liquid handling system and related devices) or other devices that employ gravitational energy, manual energy or other energy sources to transport, dispense, treat and otherwise impact milliliter through femtotliter quantities of liquids with an accuracy and the precision of a few percent and do so without or with touching launching and directing the material to the target or targets using one Gaussian surfaces or a series of coupled or joined nested gaussian surfaces which can have the same or different cross sections with removable fuses silica capillaries or polymeric coated or uncoated tips and which can exist in a singular or plurality of many similar or different coupled nested gaussian surfaces of normal, beveled or bi-beveled cross sections which may or may not be coated with conducting or non conducting materials on the body or at the tip to either enhance energy transfer or prohibit energy transfer and hence liquid movement. Such surfaces can be handheld, mounted to holders in parallel or joined into a plurality of a series of such surfaces mounted and or otherwise attached to a robotic platform of x, y and z of other geometry such that electric energy can be applied to the surfaces individually or collectively via electric induction or a blend or induction and direct wired connection to any nested surface or series of nested gaussian surfaces or to liquid contents thereof or optionally to any physically disconnected or physically connected target or targets where the gaussian surfaces or the targets can be made of nonconductors or conductors or any combinations thereof, as it uses passive or active surfaces to direct push the liquid or its parts to targets be they vessels, surfaces, instruments, food, plant, animal or human subjects or to pull the liquid to the target by charging that device or devices. Such liquid movement can also be quantified by measuring the current, optical, thermal or other parameters or metrics as they are digitized and coordinated to energy that such processes have occurred and that a record has been made.

One version of the apparatus consists of a unipolar or bipolar digital DC power supply that is uniquely sampled with a high voltage relay switch to affect rapid HV sampling optionally without varying the same, hence allowing for rapid energy sampling. This system may be arc protected, current limited and programmable and optionally coupled a RF power supply whose individual energy can be combined with the DC energy in any mixture. Such energy can be applied to Gaussian surface or other inductors such that any Gaussian surfaces or its electrically disconnected targets and its contents can via induction acquire energy. The energy system is integrated with other energy sources (e.g., syringe pumps, peristaltic pumps, piezoelectric devices, sound energy and other sources of energy in a coordinated, programmed manner to the Gaussian surfaces to effect liquid or other matter transport causing non-touch dispensing or the same with sample treatment including, but not limited to multichannel, unique dispensing, filtration, SPE, LC, electrophoresis or serially parallel derivatives thereof or instrument or other device liquid introduction in a low volume drop or spray mode that is actively/passively directed to the target and counted and recorded by electrical, optical, thermal or other means and written to a digital medium as a record that such processes occurred.

In similar simpler devices, analogue DC HV power supplies that may be arc protected, current limited and programmable and coupled optionally to a RF power supply or not, but that can apply energy using foot pedal switches or rheostats and a Variac to energize an inductor with high voltage and thereby or one or more Gaussian surfaces to perform liquid or matter movement or dispensing, LC,SPE filtration and serially parallel derivatives including instrument or device sample introduction when attached too one or more common or other devices like pipettes, syringes, capillaries, capillary manifolds, lab/chips and optionally when such simple devices are coupled to other sources of energy (e.g., micrometers or hand tools) or digital stepper or matter movement tools that can create drops, which are subsequently energized electrically and launched to surfaces. Such matter can be measured, monitored and digitally recorded as given in the previous paragraph.

While inductors can be employed in simple of complex versions of the device it is possible to employ inductors and by direct electrical connection to any or all of such surfaces where the potential can be turned on or off using a switch in a ballistic manual mode or alternatively using a selector switch and a potentiometer or alternatively an auto transformer that can be employed to apply a constant potential or that can be manually changed in a positive or negative fashion to effect a dynamic change of potential or in a programmed by mode that uses a computer or microprocessor driven circuit to drive the programmable power supply using a high voltage relay switch can sample the applied potential. In the program mode then the potential can be taken from any value V1 to any value V2 using any C++ function or series of C++ functions applied to any gaussian surface individually or collectively or to any physically connected or disconnected target or targets and do so as the current is measured by inductive or conductive processes and device (electrometer, shield picoammeter or equivalent).

The apparatus can further consists of surfaces made of conducting or non-conducting materials that can actively or passively form and direct the liquid as it emanates from the last gaussian surface prior to launching to the target or targets that may be charged or non-charged. The device may be powered by batteries, DC power or AC power of the necessary energy and current. It can be handheld single channel, mounted in multichannel mode or either of the above and any combination thereof where individual circuits or optical tools measure the amount of liquid launched to the target and measure amount of liquid that got to the target with optional computer or microprocessor data acquisition and processing to compare launched vs. received charged or other matter and to keep complete records of all such occurrence in an optional database couple to an optional expert system.

The energy of either an analogue version of the HV energy source or the digital HV energy source which may or may not be coordinated can be appended to common devices of all types like capillaries, syringes, pipettes, pumps of all types or to targets such that an induction process results in liquid transfer to the target with out or optionally with touching effecting precise dispensing and if said devices (pipette or syringe tips contain medias (SPE,LC, filters, polymers or biopolymers of immunoassay or other nature covalently or otherwise attached to surfaces or other matter), such devices can not only dispense, but they can also perform tasks like analyte isolation, sample cleanup, and other tasks with sample placement which can be onto matter (e.g., MALDI plates, humans, food other matter) or into matter (e.g., microtiter plates, vials, beakers, mouths) where current measurements of the energy process are made to verify the action, as the device can incorporate current or optical measurement technology to sense and to verify how much and when matter has been launched and how much has been received by the target or targets one channel at a time or more channels at a time and this may be optionally recorded by visual, electrical, thermal or other means.

When used in a sampling mode, the device can measure electrically or optionally optically the amount of chemical from a living or nonliving entity, and with mass spectroscopy based or optical spectroscopy based technology, said chemicals emanating from a living or nonliving entity can be sampled, detected and identified and computer records and processed.

The device can optionally consist of various options to facilitate operation and to verify the operation of this technology including: a source of light to aid in visualizing targets such as lenses and LED which may optionally be fed from a fiber optic cable; a source of laser or other light to make spots of exact, known dimensions near adjacent to targets to aid calibration via machine visions techniques such as pixel counting; a foot pedal that can be employed to apply/control the energy application to the devices or targets; a motorized plunger using a stepper motor or other device that can fit into the gaussian surface or surfaces to push the liquid to grow drops or otherwise transport or produce drops of flow for transport through media for subsequent transport to targets; coils or other current or magnetic filed measuring devices to measure the charged liquid transport through a space from a gaussian surface verifying a dispense or optionally use machine visions or current measuring techniques; such as, pixel counting of liquid blots on surfaces or video recording to further or independently verify the accuracy and the precision of liquid transport to a receiver or a surface; employ one disposable gaussian surface or more than one as the body of the device, as a tip or as the entire liquid holder; A nano or picoammeter or equivalent may also be used to quantify the liquid, solid or slurry going form one place to the next, optionally going through media of any type, where current or optical measurements quantifies the amount of process taking place, and where such information is stored in compute hardware and software for record keeping purposes of all types and which optionally includes an expert system to warn of excursions.

In another mode, Gaussian surfaces are coupled to mass spectrometers, ion mobility spectrometers or other chemical detectors of all types through an interface that aligns drops or this sampler is set to pull and detect explosives or any other chemical of interest to national and international security from people in airports or anywhere else in a non-dispersive manner. Automated software detects explosives of other chemicals including low molecular weight volatile and involatile molecules that can be used to identify disease, explosives, viruses, allergens and other entities of all types. Optionally, this method can be used to QC devices, or liquid, solid, gaseous or other products.

In another mode of operation, liquids are charged emanating from Gaussian or other surfaces using induction, conduction, or a hybrid electrical and mechanical energy transfer systems, such that charged prepolymers are launched and cooled and optionally further energized by photons, heat or otherwise of proper energy to create unique polymerized entities, chargemers, that can be used for capturing chemicals and for many other functions, creating unique charged entities for many applications.

In another mode of operation, using a programmable DC power supply, and either an electrostatic pump or other pumps of any kind, liquids coming directly coming from LC columns, SPE devices, filters, serially parallel derivatives or form pumps of any kind thereof can be charged and deposited onto surfaces for MALDI analysis or they can be fired into a charged MS interface that both pumps out neutral vapors as it heats the small liquid drops using IR or other heat sources. That interface consists of an inductor, and charged cylindrical porous surface which is also held in a concentric cylinder which is attached to a mass spectrometer and which is also attached to a vacuum pump from which solvent vapors are pumped as charged ions fly with direction to a series of differentially pumped the sections outside the MS with skimmers or holes to facilitate enrichment of the ions and exceedingly high ion transmission grater than common ESI or electrospray ionization.

Optionally, a series of selector buttons on the device or on the power unit an IR remote to control and to select the energy level and energy path of an experiment; mounted or detachable volumetric scales with lenses to visualize and measure the liquids; a charge station or stations where the one or more joined, nested gaussian surfaces can be electrically charged by direct connection to or by induction from a voltage source; assorted electrical attachments provide energy to any gaussian surface or its contents; compression and other fittings to join gaussian surfaces and disposable tips made of fused silica, polypropylene, quartz, PFTE, optionally equipped with flits, chromatograph or other media, and themselves potentially coated with PFTE, metals, polymers, or other inert or conductive material/s with or without electrical leads, a cradle that can hold the joined, nested gaussian surfaces, batteries, charging circuitry and circuitry to sense the liquid level or plunger position with alpha numeric LED and other displays, a holder or set of holders that can isolate the joined, nested gaussian surfaces from or optionally connect them to ground; compression, screw based or quick connect or zero dead volume unions to join or couple gaussian surfaces made of quartz, fused silica, polypropylene, PFTE and or coated there to with inert, metallic or non-conducting materials, Microtiter plates fit with very low volume conducting surfaces individually wired for each well and connected to a microprocessor based readout in a manner that can individually identify how much charge exist or enters any individual well at any time t using either multichannel nano or picoammeter.

In a very simple mode of operation a HV analogue power supply connected to a syringe in one or many ways is energized after a drop is manually or otherwise placed on the tip. The live voltage transmitted through a foot pedal, to a −8 kV analogue (Model No. 750 120 VAC-7.5 kV) high voltage power supply from the Electronic Goldmine power supply take any syringe part to that potential, and the drop flies to a grounded target.

The same effect can be realized when a drop is grown on a pipette, capillary or other Gaussian surface.

The application further extends IBF with mechanical means of liquid movement like a micrometer, stepping motors (e.g., MCH3, and LT35, Nippon Pulse Motor Co., LTD, Japan) with controllers singly and in groups of standalone or integrated action.

This application further extends IBF with programmable stepper motor with integrated robotic platform movement and laser spotting and position measurement and pixel counting techniques coupled with real time volume sensing and conductive microtiter plate verification of the charge and the charge received with position data and computer data compilations and record keeping and verification software/hardware.

This application further extends and invents new ways to sample living and non living entities for direct non touch, non dispersive sampling for medical and dental purposes; for counterterrorism purposes; for product liability, for medical diagnostics; for drug detection and other purposes including drug discovery, drug delivery, medical diagnostics, MALDI TOF and other sample preparation, and human or animal sampling, by simply in a non-dispersive manner pulling the odor, sweat or vapors from targets that can be humans or animals or other living creatures or entities of all kinds.

This application further extends IBF by providing electrical and optical means to measure and quantify such process, of all types N Channels at a time, as it acquires data into a microprocessor or computer or both for subsequent computer record keeping and for optional subsequent analysis by expert computer systems.

The application further extends this technology by having battery, DC or AC powered configurations which can be handheld, mounted or robotically assisted. This application further extents our technology to solids; slurries; charged and other non-charged matter when used with alternate integrated energy sources.

DESCRIPTION OF THE DRAWINGS/PHOTOS WITH EMBELLISHMENT

FIGS. 1,2,3,4,5,6,7,8,9 show pictures of three versions of the core circuitry and related devices and circuit boards used to coordinate the IBF force typically to the inductor in a programmed manner. The core device consists of an HV source or sources, an HV relay to sample the HV without varying same and inductors (energized surfaces), connectors and electronics component that allow for the digital and or analogue alignment and integration of more than one energy source (e.g., an HV DC source and a syringe pump and a robotic set up as a Spark Holland, Alias) to effect single of parallel dispensing, LC, SPE, filtration and serially parallel derivatives thereof including device or instrument introduction. When such a system is fitted with current, optical, thermal devices, the liquids can be launched to a lower energy target as it is actively/passively directed by the inductor or other surfaces where functions are optionally performed (LC, SPE, etc.) one and a current, optical or thermal record is mare thereof.

Optionally, an inductive, conductive approach can be used. They include basic design elements the include EMCO HV power supplies (Sutter Creek, Calif.), HV read outs (V1G, EMCO) and HV relay switches (EMCO) to uniquely sample the HV without shutoff. A home built 16 bit microprocessor is used to control the system using C++ code drive that reside here and it allows the value of the HV to be changed from one value V1 to value V2 over time t1 to t2 and as such the HV is sampled by flying leads that are ultimate connected to the fluidic inductor and that is coordinated with other sources of energy like a syringe pump to program the liquid launch direction chemical process and liquid to a target.

This device also employs shows and LCD shown in other pictures of this device whose complete command set allow for completely automated or "manual" operation.

FIGS. 1 and 2 show the circuit board and the open back of the Digital Nanoliter Cool-Wave, version 1.0.

FIGS. 3 and 4 show version 2.0 of the Nanoliter Digital Cool-Wave Version 2.0. The lay out is significantly different and it does not use LCD. Moreover this device communicated with a PC via and RS 232 port and with communications and programs or scripts (Attached in the program Appendix) that are interpreted using Docklight (Germany) software.

FIGS. 5, 6 and 7 show three different views of The Digital Nanoliter Cool-Wave, Versions 3.0 which uses a smaller foot print, but is functionally similar to version 3.0.

FIG. 8 shows another versions where using two sources, one can perform pulsed positive ion, negative ion liquid induction experiments can be conducted to create charged liquids on different positive or negative polarity in a programmed manner. In all of the above the energy is provided to the inductor or optionally the target through shield flying leads. Alternatively, inductive surfaces can be employed like a parallel plate capacitor.

Figures show different liquid inductors which consist of a shield HV lead (Alden, Brockton Mass.) and in this case a tube (Needle injector tube, Spark Holland, Emmen The Netherlands), a PEEK union (Upchurch Scientific Oak Harbor Wash.) which has a 150 micron Teflon fused silica tube of varied radii dimension, 3.5 cm long and or optionally a shorter tube of the same radii fitted to a quartz GC compression union (Polymicro Tech, Phoenix, Ariz.) and more Teflon coated FS to effect the 3.5 cm length, but to provide an easy way to change tips. This device can has a metallic induction union (1.5x,¼", Home Depot, LV,NV compression fit onto the end of the union to which ultimately the HV lead is attached. This assembly is fitted into polystyrene tube that can optionally be painted with RF/DC damping paint or materials too reduce EMI. The large tube has an entry point for the HV flying lead, and optionally the large cylinder can have tubes that provide for the input and the removal of gas to affect stable dispensing but managing the atmosphere above the target, or by removing the vapors, or both.

FIG. 9 shows tow versions of the inductor.

FIGS. 10 and 11 show different views and drawings of how the inductor can be used.

Figure 1:
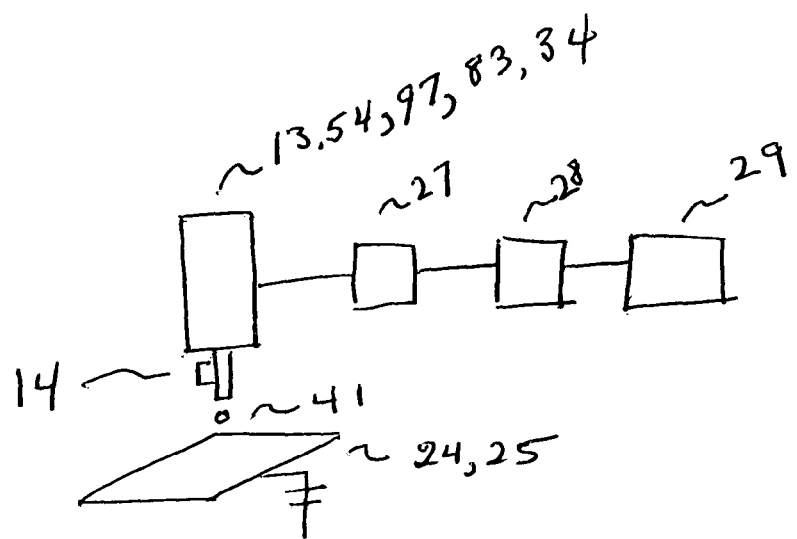
Figure 2:
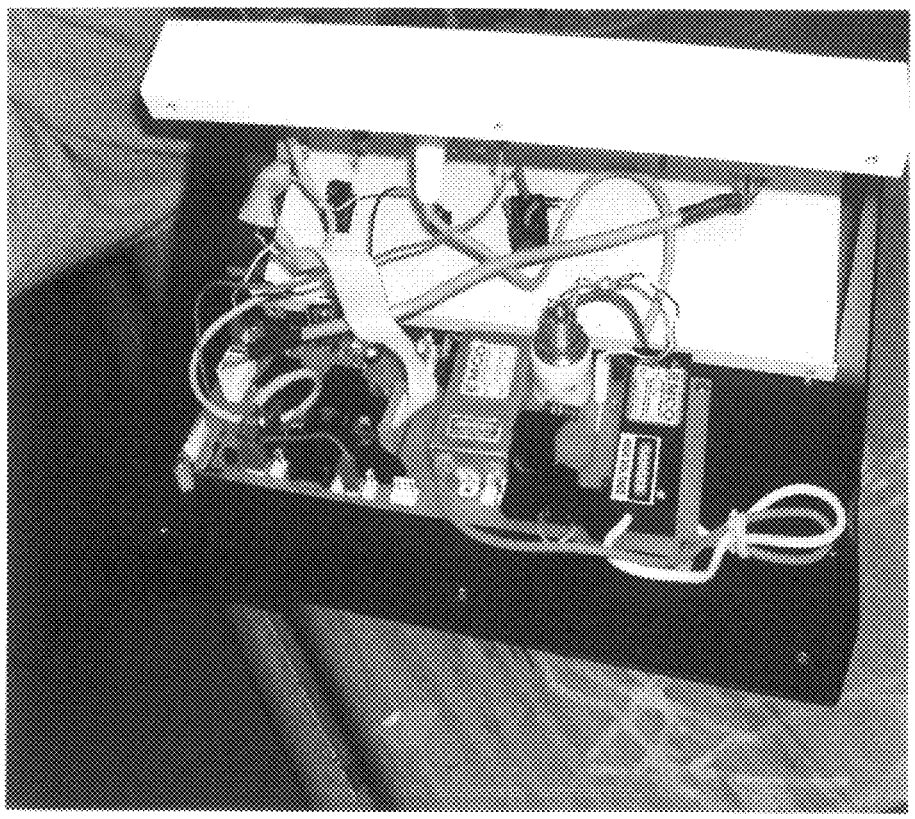
Figure 3:
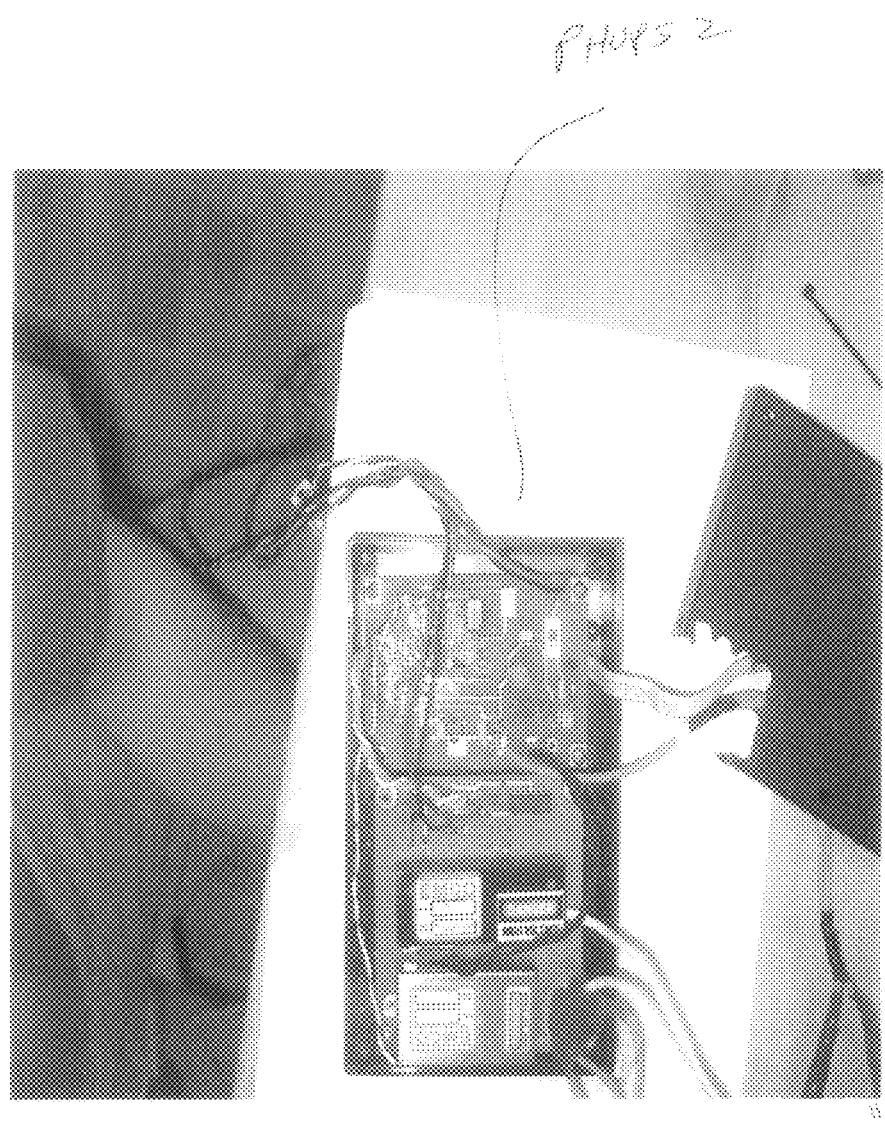
Figure 4:
Figure 5:
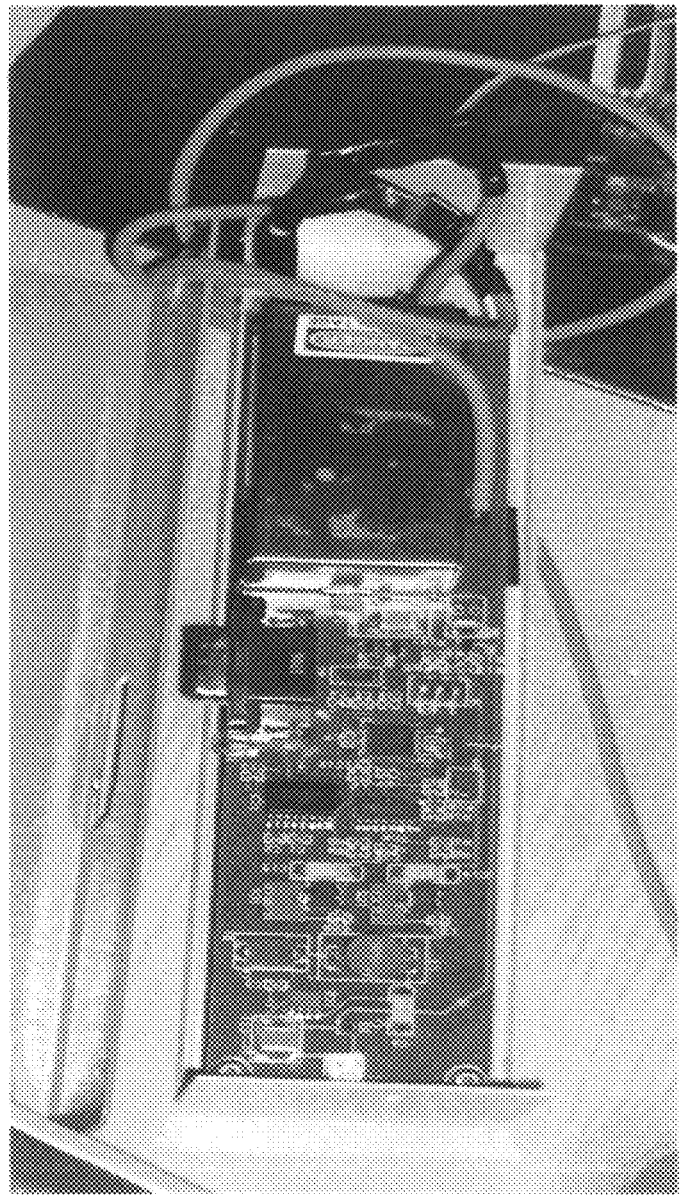
Figure 6:
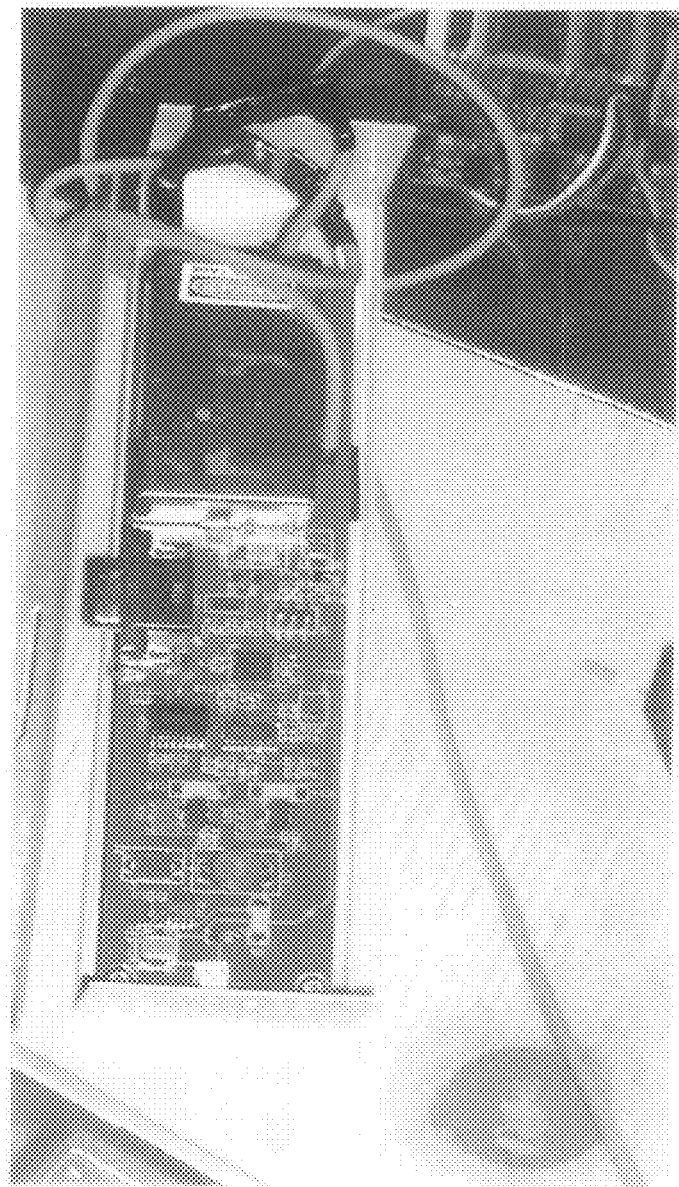
Figure 7:
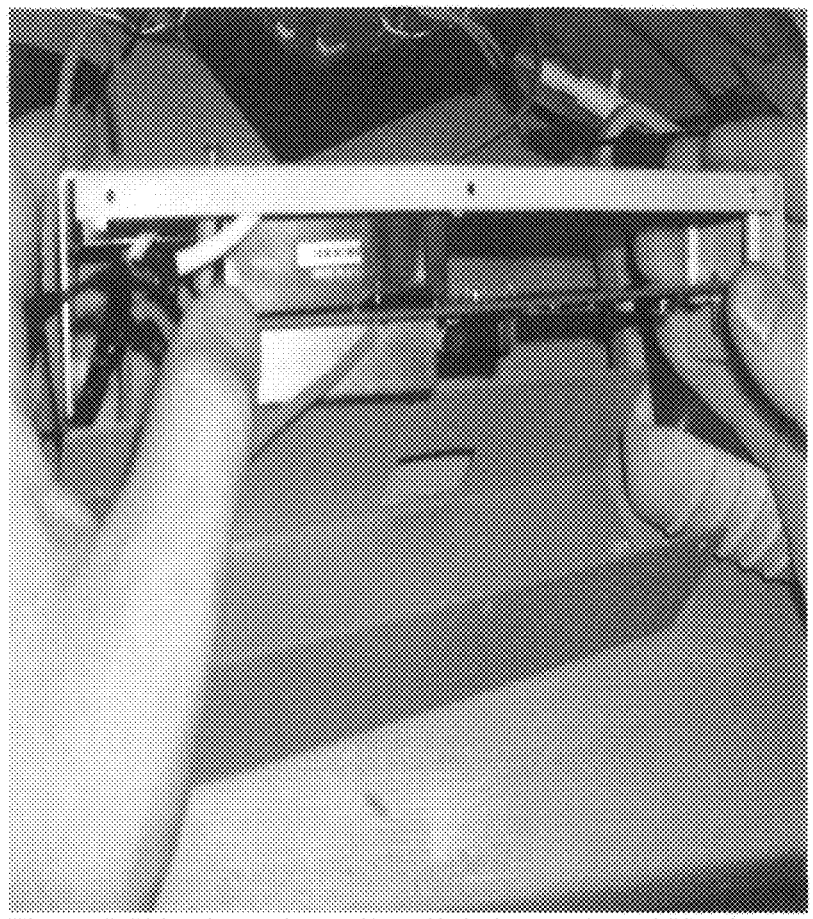
Figure 8:
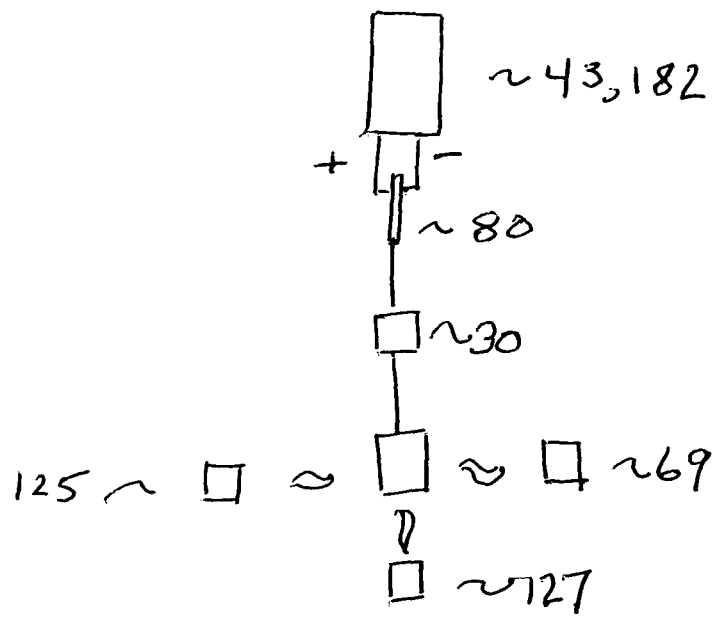

The inductor being connected to the HV lead of for example, the flying lead of the Digital Nanoliter Cool-Wave, Version 3.0. HV FIGS. 12 and 13 show the Spark Holland Alias (Emmen, The Netherlands) and an inductor above a 384 MALDI plate (ABI/MDS Sciex, Ontario, Canada) with nanoliter drops dispensed in an automated matter from version 3.0 of the IBF circuitry.

FIG. 14 shows the Alias connected to the Version 1 of the Digital Cool-Wave. This arrangement was used in an "manual" manner to allow us to develop the inductor.

FIGS. 15,16,17,18,19, 20 and 21 show pipette based aspects of IBF where either a "manual" (FP=foot pedal) analogue HV or a digital automated HV power supply supplies energy to one or more channel pipette, where the current can be measured by various devices too verify dispensing. It is important to note that either the device can be inductive charged or the target can be charged.

In FIG. 15, a P2 pipette is shown using the proprietary patent pending tip along with the inductor stand, conical charging station (single channel in this case) with circuitry that can energize the liquid to fly form the tip to the target and measure that current with a circuit and other devices using HV protecting circuitry.

FIG. 16 shows another version of the nanoliter pipette which can use be analogue or digital HV power supplies previously indicated herein and current measuring circuitry to measure volume.

FIG. 17 is shown as an 8 channel dispenser with an inductive holder which can measure N channels at a time using Keithely card 7053 systems and programmed electrometer or picoammeter. This device shows a dual capability both a digital and an analogue option using a HV switch to select on of the other option.

FIG. 18 shows another variety of the nanoliter syringe with single or 8 channel options in analogue or digital mode. This variation shows the ability to use DC, RF or RF/DC energy systems dispensing into a microtiter plate with or without robotic movement.

FIG. 19 shows a motor driven air compression device dispensing a liquid to a tip. In this case the metal plate is charged by the analogue HV −8.0 kV device and foot pedal to effect dispensing of nanoliter onto the plate.

FIG. 20 shows pipette accoutrements one being a method to punch holes in pipette tips (to allow for the aspiration of the liquid in capillary tips) and another 8 channel pipette inductor.

FIG. 21 shows a wide variety of IBF pipette tips. These tips can be made by threading fused silica capillary of 360 micron diameter (Polymicro, Phoenix, Ariz.) into the capillaries being held on pipette tips, Plastibrand of Germany, 100 uL or 20 uL to which a hole has been made to which one can realize a tight compression no leak fit. These tips can optionally be coated with conducting paint or other material to assistance charging on the body or the tip or they can be coated with nonconductive coating to assist dispensing, but to eliminate faradaic processed. Using these the tip on the pipette is placed into a liquid whereupon capillary action picks up a known volume of the liquid given the known length and diameter. Then the pipette is taken and pressed into the induction stand whereupon the pressure forces the liquid to the tip by that pressure an optionally pressing the pipette button. The liquid is held on the tip due to the forces of adhesion and cohesion where upon energizing the induction stand the liquid flies onto or into the target of interest.

These tips can be coated polymers of all types including one or a plurality or materials and layers at the tip only and that tip can be deactivated with alkyl groups to activated with OH or other groups. The capillaries can have concentric holders are colored coated to know the volume or optionally, the tips can have lines on them that are colored coated to show where they should be cut to yield a given volume. These tips can also use the quartz GC union to facilitate sample handling and dispensing (Polymicro Technology, Phoenix, Ariz.).

FIGS. 22 through 30 show microliter syringe based application of analogue and digital IBF.

In FIG. 22 one sees the manual nanoliter microliter syringe which consist of a Starret (Els,NJ) or WPI (Sarasota, Fla.) micrometer (SPG-KIT-MICRONR) micrometer and an patent syringe coupler which contains a 701 Hamilton 10 uL syringe (Reno, Nev.) in a form fitting inductor (home built) on a based polymer base. An HV leads. This lead connects to either an analogue Nanoliter Cool-Wave or any digital Nanoliter Cool-Wave.

Figure 23:
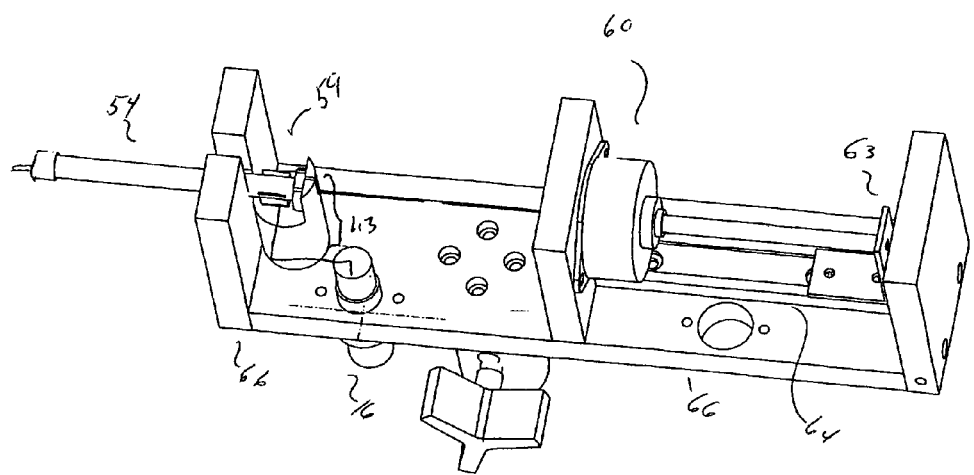
Figure 24:
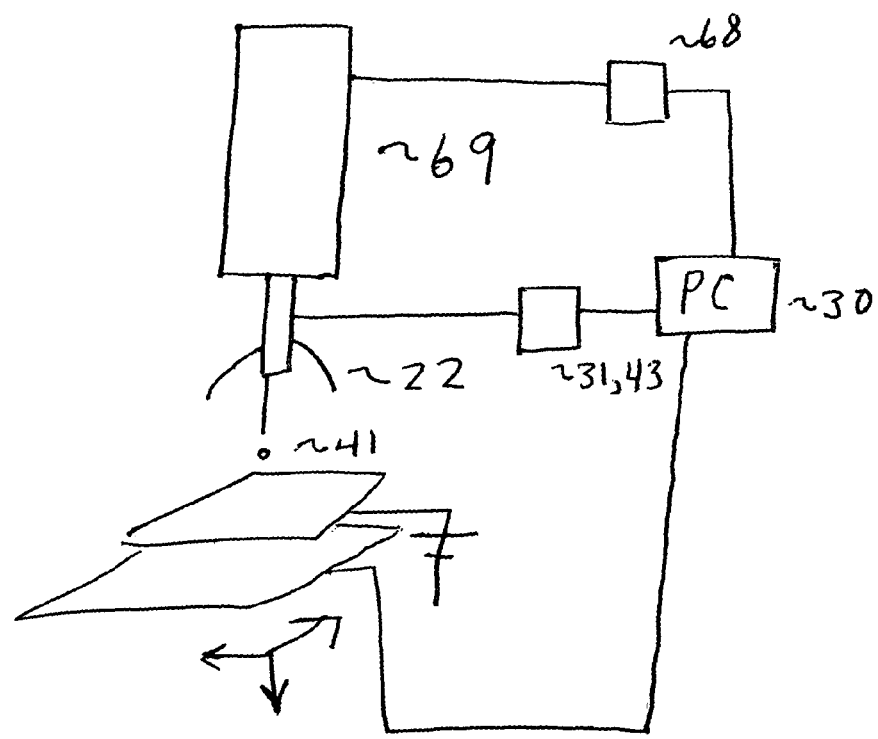
Figure 25:
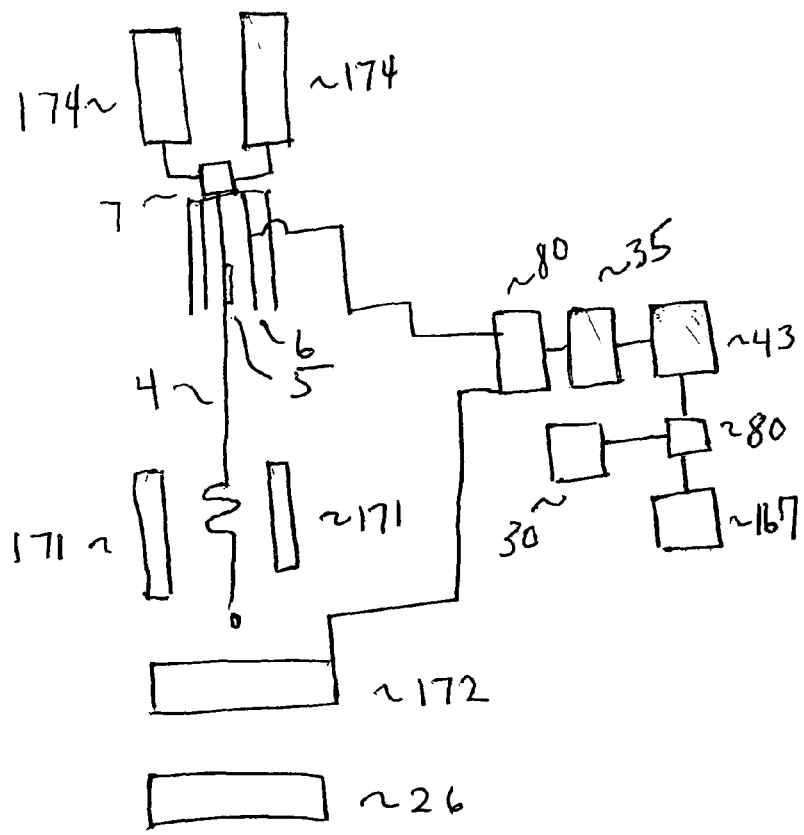
Figure 26:
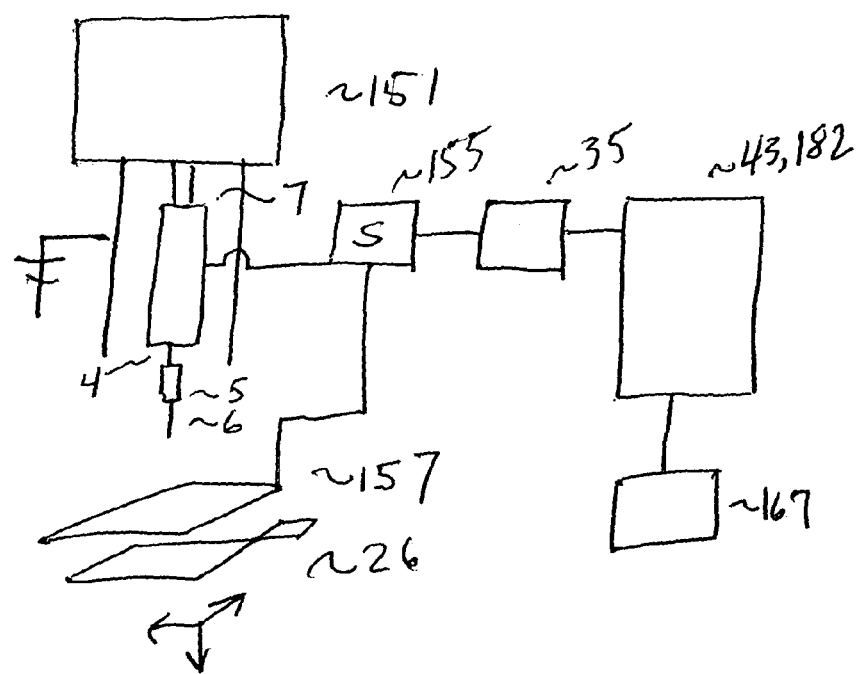
Figure 27:
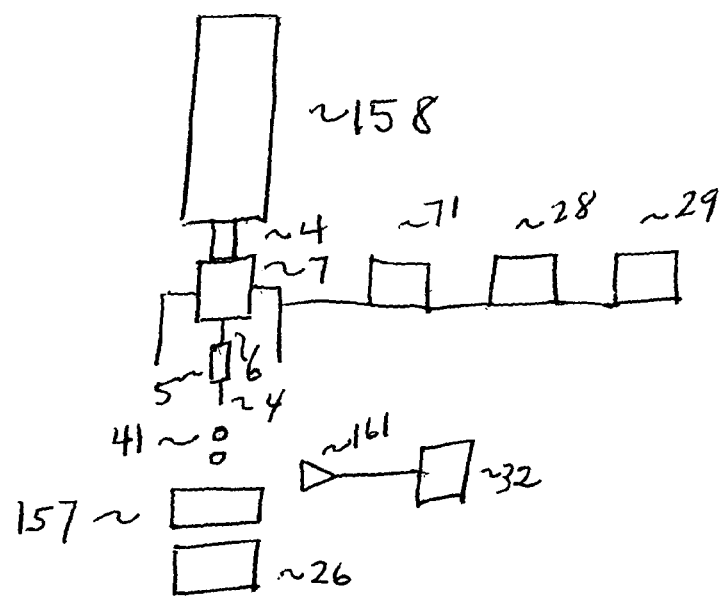
Figure 28:
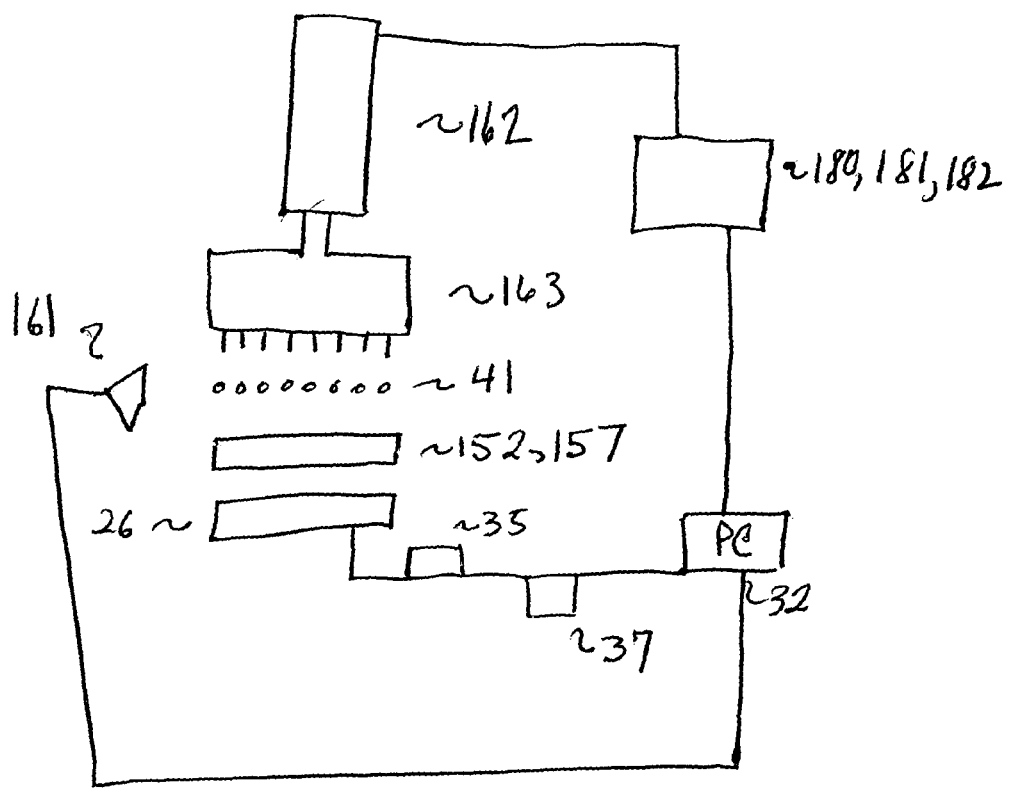

In FIG. 23, an automated digital syringe movement device is shown consisting of a stepper motor (and controlled controller not shown), microliter syringe, HV leads an conducting energy transfer systems including hand tightening and an encapsulating box.

FIGS. 24 through 28 show various embodiments of the automated nanoliter syringe.

Figure 29:
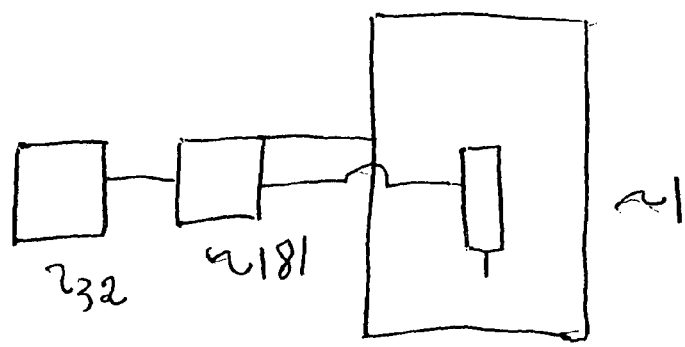
Figure 30:
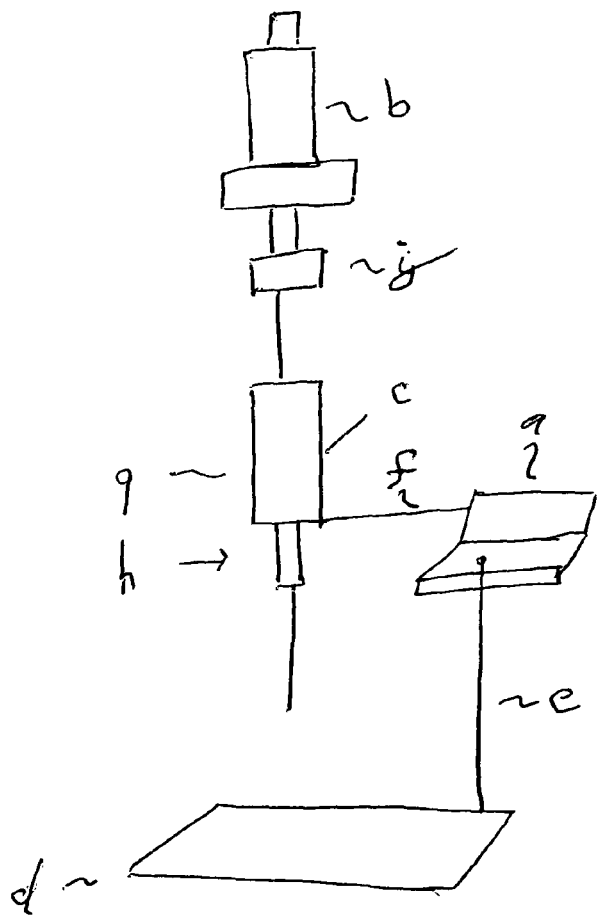

In FIGS. 29 and 30 we show another version of an Nanoliter Analogue Cool-Wave which includes the −8.0 kv analogue power supply that is the, a nanoliter microliter syringe as described previously holding devices, a foot pedal (Tolly, Cern, Switzerland) and showing a microscope which is no apart of this patent.

FIG. 30 shows that this manual syringe can be attached to x,z moving robotic stage and attached to our original Nanoliter Cool Wave version 1.0. Here sample and liquid movement is manual and the liquid energizing moving part can be "manual" or programmed.

FIGS. 31 and 32 show respectively a zero dead volume union made from concentric tubes of heat shrink polymer (Zeus, Orangeburg S.C.) which is useful for joining lumen of all type.

FIG. 31 shows two tubes where one is surface deactivate with for example alkyl groups and another tube that has a metal coating at or around the tip, but that is also surface deactivated such that the dispensing of polar liquids from inductors can occur with greater facility and to lower levels.

FIG. 33 A, shows an 8 fold manifold that can be placed onto a microliter syringe to allow for parallel dispensing.

FIG. 33 B shows the metal syringe coupler that is used to couple a syringe plunger to micrometers or stepper motors.

FIG. 34 also shows that top and side views of home built electric induction based sensors to measure liquid transit.

FIG. 35 shows and an IBF, pure induction glue dispenser which could optionally be employed in an inductive, conductive manner.

FIG. 36 shows one current measurement device.

FIG. 37 shows a parallel LC system that has parallel liquid isolation valves.

FIG. 38 shows one parallel LC manifold.

Figure 39:
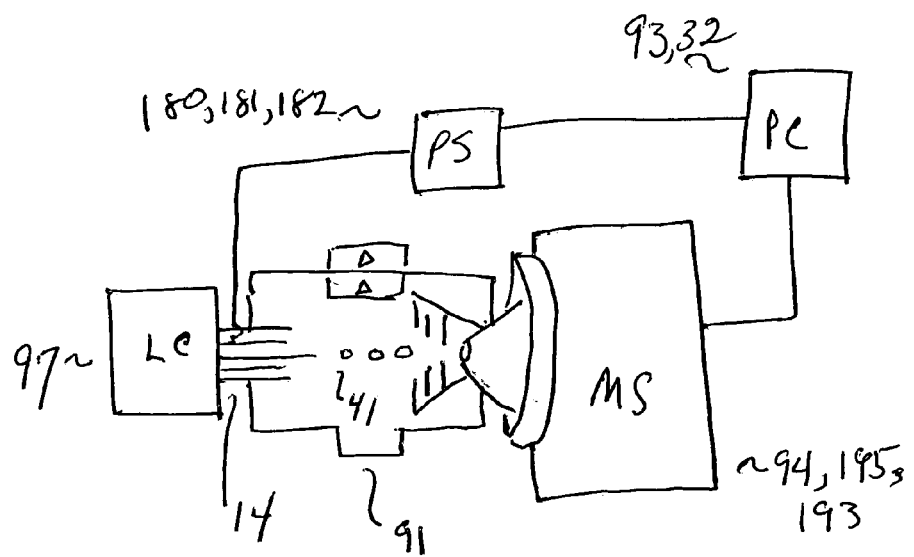

FIG. 39 shows a device that uses IBF and a our third generation circuit to place ESI and ions into mass spectrometers and other instruments with high enrichment.

FIG. 40 shows a human sampling device to place human or other chemical into a MS or other instrument of any type.

FIG. 41 shows an array of syringe devices and accoutrements.

FIGS. 42 and 43 shows and IBF way to cool human beings and other entities.

FIG. 44 shows a handheld nanoliter syringe which employs a 10 uL or other microliter syringe (Hamilton Company Reno, Nev.) that is attached to a frame with a Thorlabs (Newton, N.J.) C clamp and a –8 kV analogue (Model No. 750 120 VAC-7.5 kV) high voltage power supply from the Electronic Goldmine is likewise attached with a switch (e.g., a GC miniature Bat handle toggle switch 35-004 or equivalent) and foot pedal switch or a foot pedal rheostat (http://www.brandsonsale.com/ht-001500.html) with lead to line voltage. The 701 Hamilton or other microliter syringe has a modified tip which consist of a shortened regular tip coated with 2 mm heat shrinkable Teflon tubing (0.5 cm, Zeus, SC) and a quartz GC union and regular fused silica {of all types} or modified tips (Polymicro Tech, Phoenix, Ariz.). The device has a normal plunger or an optional small low throw micrometer taken from e.g., a C-Type out micrometer from ABS of China, part number 200-0150, 600-c011 to move the plunger and using one of our machined metal or non metal couplers. To the frame is placed a hand fitting handle.

FIGS. 45 and 46 show a wide variety of tips that can be employed in IBF or other dispensing technologies. Often any type of fused silica with any type of standard or other coating or covering (e.g., polyimide, perfluromers of any type, silicones or any other polymer) can be employed (Polymicro Technologies Phoenix, Ariz.) to facilitate liquid deposition. Having precise radii and being of known length, such fused silica or quartz or other Gaussian surfaces can have cylindrical covers or sleeves made of PEEK (Upchurch Scientific, Oak Harbor, Wash.) or Teflon and other normal or heat shrinkable polymers (Zeus, Orangeburg, S.C.) that are color coded to facilitate the identification of and the handling of these tips accurate volume tips by humans or robotic devices. Each fused silica or other cylinders (that can be made of a polymeric, quartz or other materials can have multiple colored coded lines to facilitate the production of known volume entities while in use by cutting at those lines with sharp objects (See figure showing Exact volume color line {EVCL})see. Each Gaussian surface can be optionally laser cut to insure precise volumes acquisition and liquid handling or dispensing and each of those may be appended to a quartz GC compression fitted union (Polymicro Technologies, Phoenix, Ariz.) to afford multiple different types of know volumes to emanate from any liquid transfer device produced by Nanoliter,LLC or other firms. The surfaces at the distal end can be treated with trialkylhalosilanes and heat, perfluoromers and any other surface modifying chemical to deactivate and reduce surface adhesion and to facilitate low volume dispensing. Optionally the same tubes can be coated with conductive material of any type in any manner to facilitate inductive or conductive energy transfer to the liquid or tube. Such energy transfer devices can include.

Pointed tips like those manufactured by New Objective (Woburn, Mass.) or u-Tips World Precision Instruments (Sarasota, Fla.) for electrospray and other applications can be used exclusively with the GC unions (Polymicro technologies, Phoenix, Ariz.) to facilitate low volume liquid or matter transfer.

Such devices can be directly made into circuits using DC,RF,DC/RF energy for dispensing using analogue or digital devices shown and described herein. These devices can be energized or at ground potential energized at the tip, the body or at the target to effect matter movement. Metal or conducive tipped capillaries or Gaussian surfaces can have a monolayer of conducting material and be covered with a nonconductive surface to insure that there are no faradaic processes involved in the transfer of liquids to targets.

In FIG. 47, we show a microliter syringe as previous shown in this an other applications, but that has an HZ or optionally another switch to allow for the application of BOTH inductive and conductive energies to the liquid or other matter in the body of the syringe or elsewhere.

FIG. 48 shows an 8 channel nanoliter, microliter syringe made form a standard 10 microliter Hamilton Reno Nev. syringe that has been fitted with a modified tip and quartz union and a 8 fold or manifold, and 8 quartz GC unions to which fused silica paths or capillaries are attached and which as described previously and inducting or conducting wires or leads that are connected to a two or three position HV switch to select the energy path to either the syringe, the target or to analogue or digital HVPS for 8 channel or n channel dispensings.

FIG. 49 shows nanoliter, microliter syringe made form a standard 10 microliter Hamilton Reno Nev. syringe that has been fitted with a modified tip. In this application the glass barrel of the syringe has been bored out to fit a Teflon based compression union and a BD, 150 micron fiber optic cable joiner so that a fused silica or other tip can be placed in and removed face-lifting dispensing of nanoliters.

FIG. 50 shows syringe, pipette and pumps of all types and the electrical manner to connect them through switches and otherwise to RF power supplies to effect matter transfer. Note each matter holding device can be operated without the other.

FIG. 51 presents both chip based and plumbing union based 8 folds that can be employed to transform a single channel syringe or device into an N channel device.

Figure 52A:
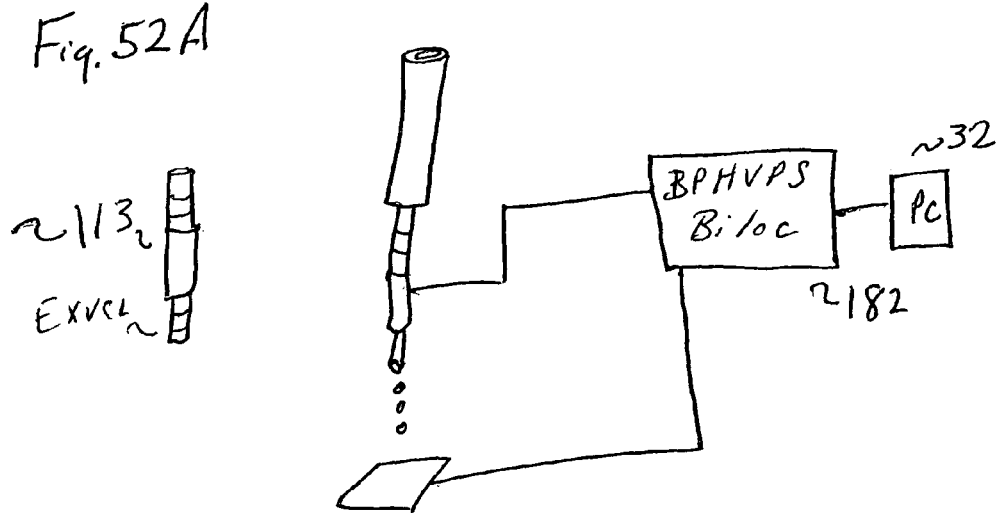
Figure 52B:
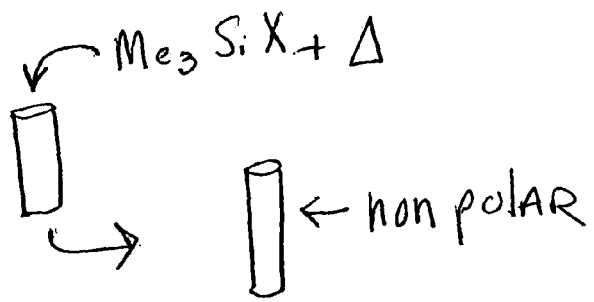
Figure 52C:
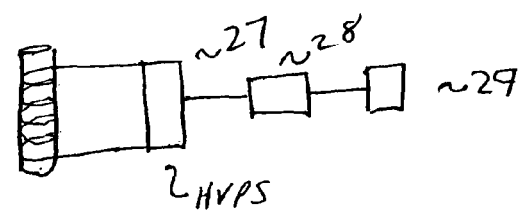

FIG. 52 is nL, uL, pL modified N channel pipette with dispensing tips and inductive conical charger and energy supply with 10 slot Switch (7002 Keithely), electrometer and PC with 8 fold paths, HV supply and sensors with Faraday cups and a low current Scanner (7058 Keithely) for current measurement. The device consists of normal 8 channel or more channel pipettes where the energy can be placed on the holder or the pipette.

DETAILS

With enhanced induction based fluidics, femtotliter to milliliter volumes of the same or different liquids or related matter are electrokinetically dispensed, treated, introduced or transformed singly or in parallel alternatively using a hybrid coordinated energy approach such that volumes of liquid or other matter are dispensed, treated, introduced using electrokinetic and programmed, coordinated, i.e., integrated alternate or composite energy sources such as electrical energy plus, mechanical pumps, peristaltic pumps, piezoelectric driven pumps, composite ultrasonic and thermal driven pumps, siphons, pistons, gravity or other manual energy sources such as plungers and other energy sources to effect individually or in a highly parallel manner to various effects on matter using a simple, but powerful effects with apparatus like capillaries, syringes, pipettes, pumps, hybrids thereof and more complex devices; such as lab/chips, mass spectrometry interfaces; ammeters and complex parallel electronic circuitry current measuring circuit and fluidic circuitry and accoutrements (e.g. normal and inductive or conductive holders and/or pipette and syringe tips of diverse types, manifolds of different types, inductors of diverse types and other liquid holding devices like the single and parallel hand held pipettes, capillaries arrays and more.) to move matter, move and treat matter, move and treat and modify matter or to move, treat and modify matter to various local effects like cooling compartments and other entities, or to effected instrument introduction and also effect such processes optionally are measured and verified by optical, electric, thermal or other means and as such information is recorded and placed into databases and other record keeping forms. Such IBF and related technology can range from an energized capillary to simple electric pipettes or syringes to very complex parallel LC/MS/MS sample analysis and introduction devices.

In such devices inductors are employed to impart energy to the Gaussian or other surfaces alone or in conjunction with conductors or any other energy source used with liquids. In these embodiments, standard and modified nested Gaussian surfaces or derivatives such as capillaries of any type, syringes, pipettes, pumps of all types with single or multi-channel attachments or manifolds, microfluidics chips, disposable plastic or other Gaussian or other surfaces are employed to hold and to transport or project matter of any type to targets of all types (humans, plants animals, inanimate objects of all type) and materials, were energy applied is optionally DC, RF, DC/RF or other power energy sources in a hybrid mode with or without these sources including piezoelectric, sound, heat, pressure or any other energy source in any combination to effect electrokinetic liquid, solid, slurry, glues, high viscosity or other material movement and or movement with optional liquid treatment or purification one channel or many channels at a time in any serial way or any serially parallel manner, where such entities go from one locale to another in one step or in a multitude of such steps where such movement is measured simultaneously via electrical, optical, spectroscopic or other properties of the fluid or solid or other composition of the target or moving entity optionally using any type of Gaussian or other surfaces from disposable tips coupled to fused silica via compression unions made of conducting or non-conducting other tubes in any manner with polymers of any type and or conducting materials or coatings of any type to effect or hinder inductive as selected, conductive, inductive or other energy transfer from factional frequency Hz to many Hz in handheld, mounted or a robotically assisted manner, N channels at a time where each channel can be independently configured and measured either collectively or individually such that the amount of process is measured and determined as the entity directed to targets a short or long distance ways using the energizing electric or other (e.g., gravity) fields optionally in a controlled atmosphere and optionally using proper isolation technology from a Faraday cage to other high technology EMF shielding devices as all measurements are logged in and placed in a database or other computer based form for record keeping or other purposes.

The device or devices afford ways to transport, treat, isolate, monitor, manufacture, sample, introduce, create, modify and otherwise process, manufacture, transport liquids, solids, slurries and other physical entities one or many channels at a time sequentially, sequentially in parallel or via any other paths from one place to another, or form one device or entity to another as properties of the entity are optionally measure, quantified. logged in and categorized for any desire purpose including but not limited to: sampling of human tissues or any other parts of humans for disease or for any other purpose; manufacturing electronic components; MALDI TOF and other biomarkers or disease analysis of any type; tagging any material of any type for identification or any other purpose; parallel LC; parallel SPE or filtration of dispensation or serially parallel derivatives thereof; scientific instrument introduction; drug delivery; manufacturing of electrets; chromatographic media and phases and other charged polymers; drug analysis of chemical identification to and from microliter plates; TLC and other sample placement; liquid/s dilution; liquid dispensing or sampling from capillaries; manifolds; Lab Chip devices; syringes; pipettes; microtiter plates; vials; beakers; capillary LC or any other columns; any other liquid or solid holding device of hybrid holding and treatment device (SPE, filtration or other devices or manifolds); drug manufacturing; gluing; product manufacturing; in home drug analysis or in home medication preparation; application of makeup or drugs or skin treatments; painting anything; blood alcohol sampling and analysis; detection of explosive from humans, plants; animals; luggage; cargo; device cleaning; air purification and cleaning; baking; chemical sample preparation for chemical analysis; optic repairs; lens manufactures; dynamic optical focusing devices; stem and other cell collection and movement; and other applications.

In a Pipette manual embodiments, a single channel Gilson P2 pipette or an 8 Channel P8 Gilson 8 channel pipette (Madison, Wis.) is connected to a one channel or 8 channel holder with conical conducting surfaces set at 9 mm apart center to center containing a conical conductor connected to a −8 kV analogue (Model No. 750 120 VAC-7.5 kV high voltage power supply from the Electronic Goldmine,) low current power supply which is connected to a foot pedal and line voltage. Optionally, one could employ the digital circuits HV power supplies versions 1, 2 or 3 presented above that employ an EMCO low power C80N or C80 programmable high voltage power supply and EMCO relay switches, to effect programmable computer driven operation plancg the energy on the same conical inductors.

Now with the appropriate induction tip on the P2 in a single channel version (These tips can be made by threading fused silica capillary of 360 micron diameter (Polymicro, Phoenix, Ariz.) into the capillaries being held on pipette tips, Plastibrand of Germany, 100 uL or 20 uL to which a hole has been made to which one can realize a tight compression no leak fit. (These tips can optionally be coated with conducting paint or other material to assistance charging.), it is placed into a liquid whereupon capillary action picks up a know volume of the liquid. Then the pipette is taken and pressed into the induction stand whereupon the pressure forces the liquid to the tip by that pressure an optionally pressing the pipette button. The liquid is held on the tip due to the forces of adhesion and cohesion. Now, in the analogue device, the foot pedal connected to the analogue HVPS is pressed charging the liquid which then seeking ground flies, to the grounded target or he lower energy target which can be a grounded MALDI plate, a microtiter plates, vessels or surfaces of any type and a grounded MALDI plate with tissue slices on it or other surfaces.

The same result can be realized with a digital controlled device using a circuit version number one, two or three that have been presented earlier and whose energy and direction is controlled from a PC executing the commands and the programs attached hereto.

Alternatively, the same operation as given above can be performed using an Gilson 8 channel pipette and a built eight channel inductor stand placing nL, uL and pL quantities of liquids onto surfaces, tissue, or into microliter plates or nay other vessels including small, and large ones.

The same operation can be achieved and while the current is measured to verify dispensing by using a HV protection circuit and a Keithely (Cleveland, Ohio) picoammeter or electrometer attached to ground side of the circuit. In the analogue version of this device, the pipette is placed into the inductor and the dispense pipette button is pressed as the foot pedal is pressed and the liquid drops with its charge to the conducting plate where the current is passed through an optional HV protection device/circuit (e.g., a HV resistor) into the Keithely picoammeter, electrometer or in an other current measurement device.

A similar pipette result can be realized using 3D robotic platforms.

Alternatively in an 8 or N channel pipette embodiment of the above, a Keithely scanner card system 7053 is used to house 8 or N current measuring circuits concurrently being measured subsequently by the above devices and stored on a PC.

In this embodiment, a standard one microliter syringe is connected using an alligator clip or equivalent via the non-conducting glass barrel to a current limited, high voltage power supply that is connected to a source of power and that has an on off switch. The plunger is manually depressed and a bead of liquid is grown on the tip of some nanoliter volume. Whereupon turning the switch on to charge the liquid and upon placing a grounded human finger within approximately 1 cm of the drop, the drop launches or flies to the grounded human target thereby dispensing the liquid, liquid drug or other liquid to a human target without touching the human. Similar approaches work for food, plants, animals and other grounded targets.

In a similar embodiment, the exact experiment is setup as above, but in this case the target is charged which in this case is a metal MALDI plate. After expressing a drop, to the tip of the syringe, and upon charging the target, liquid flies again to the target in this case the energized MALDI target.

In another embodiment, tubing connected to a standard syringe pump flows to a PEEK union which has a piece of PTFE coated fused silica capillary placed at the dispensing end of the union and to which a grounded metal plate is connected. Directly below which is a conducting plate of same geometry which itself is connected to a line source of energy (e.g. 120 or 240 v), a high voltage power supply and switch and upon which a grooved piece of dry ice 1 cm thick is placed. As the syringe pump is turn on and as it feeds liquid to the capillary, a drop grows on the tip of the capillary whereupon turning on the high voltage power supply simultaneous charges the liquid and attracts and drops it to the dry ice. Upon turning off the pump and the high voltage power supply, the now frozen spherical drop being charged can be literally aspirated or picked up by a charged, cooled metal rod or a charged, cooled non-conductor just a charged comb can pick up small pieces of paper.

In another embodiment, 8 LC columns of any type are connected to high pressure LC pump via a manifold and tubing. The LC columns are individually injected via either capillary action or pneumatic techniques prior to connection to the manifold with sample. The eight columns are placed into a threaded ground metal plate using PEEK unions (Upchruch, WA) and to the manifold where the columns are separated by 9 mm. Below this is another conducting plate of approximately 25 cm×m10 cm which is placed on a robotic stage that can move in one direction. The upper conductive plate holding the LC columns is held by non-conductors like an acrylic plastic that also has a one direction of robotic movement (e.g., vertically); such that, it can change the separation between the ends of the LC columns and the lower plate. The lower plate is also connected to a programmable bipolar, current controlled and current measuring high voltage power supply (Ultravolt V3, NY) which is connected to electronics that drive the power supply and which are connected to a microprocessor that drives the controlling circuitry which can be programmed from download C++ programs using and C++ function or series of C++ functions to change the voltage applied to the charging plate as any function of time.

As such, with the injected LC columns (PRP1, Hamilton, Nev.) in the manifold, once the LC pump is turned on, and parallel LC ensues, the applied potential to the charge plate can be taken to some voltage such as +2.5 kV for 4.0 sec. and then square pulsed to +3.0 kV for 0.9 sec whereupon the voltage is reset to it's original value or +2.5 kV noting that the upper plate is at ground potential. As each program is executed, the LC columns placed a few mm above the charging plate is moved horizontally by 2 mm every 5 seconds placing such drops in a temporally aligned and spatial tight row for applications including, a MALDI target production for subsequent MS analysis by MALDI TOF MS for disease diagnosis, biomarker identification, polymer analysis, surface analysis or other applications. The same approach can be employed to produce spotted tissue, for tissue MALDI.

In another embodiment of this technology a piece 20 cm piece of fused silica is placed into a liquid which contains a mixture of fluorescent chemicals, optionally liquids containing quantum dots based chemicals or other chemical species effecting a siphon. The tube of diameter 20 microns is attached to a charging plate and that to high voltage power supply and held above a grounded metal plate that rides on a robotic stage upon which targets such as pills, labels, food, identification materials and other targets are placed. When such targets are beneath the dispensing tip, the HV supply is energized dropping the liquid onto the grounded target for later identification or other purposes. Optionally, such dispenser or dispensers can be taken to high voltage (e.g., 15 kV) effecting a spray or a coating for a variety of purposes. Noting that as the liquid is not in touch with conductors, there can be no adverse electrochemistry, i.e. faradaic processes.

Another embodiment of the device is as a motorized syringe which has a plunger connected to a motor (Nippon-pulse, Japan, 35ht) that drivers the former and with other accoutrements which can grow small drop using the low micron movement capabilities of the motor on a tip of fused silica or quartz and from which drops can be subsequently launched without touch or with touch drops to targets. Such a syringe is held in a plastic enclosure that contains other options including: a light to see the liquid, a laser pointer with focus for placing spots of known dimensions on targets for subsequent analysis by the video camera or jpgs resulting from vision analysis software output (National Instruments, Austin Tex.), a lens system to manually see the liquid and to read the scale, micro switches to display/select functionality via an IR remote or direct connect line to the base instrument, an LCD panel to display the volume or plunger locations or both, an LCD display to present syringe status and options, and optional rechargeable batteries on board and a power cord. This embodiment can also have an optional charge base made optionally or either non conductors such that charged drops expressed on the disposable tips can be literally flown to the charged grounded target non-conducting targets in a manner similar to how water drops are attracted to charged tube based TV or computer monitors.

In a syringe embodiment of the device there is a charged station where standard Hamilton (e.g., a Hamilton 701RNFS 10 uL syringe with the fused silica tip cut to 4.0 cm or with an alternate fused silica tip coated with PTFE) or other microliter syringes or containers containing liquids (e.g. 150 u capillaries with 146 u fiber optic plungers) can be placed onto conducting cradles. Such cradles are covered by non-conducting lids. Whereupon turning on an inexpensive, current limited the high voltage power supply connected to the cradles that hold the syringes or containers that contain liquids, charge the liquids therein. Subsequently, upon turning off the power supply, the devices can be removed by a gloved or non-gloved but not grounded human. Where upon manually expressing a drop to the tip of the syringe, and lowering it to a grounded surface, the drop flies to the grounded surface or target. This action can be repeated as long as the liquid remains charged.

In another syringe embodiment manually aspirating a liquid into a Hamilton (Reno, Nev.) 701RNFS 10 uL syringe with the fused silica tip cut to 4.0 cm or with an alternate fused silica tip of the same dimensions coated with PTFE that is handheld by a non-grounded individual or by one wearing non-conducting gloves or alternately can be placed in a non-conducting mount like Panavise, (Reno, Nev.) is directly connected to the non-conducting body of the syringe via alligator or via an insulated HV shielded wire to the Teflon cap such that the conducting wires are not exposed, is connected to a Model No. 750 120 VAC-7.5 kV high voltage power supply from the Electronic Goldmine, which is connected to an autotransformer (e.g., Staco Energy Products, Model No. 3pn1010) which is connected to normal 120 v line voltage.

With the liquid in the syringe and manually expressing approximately 200 nL, and taking the device to 50 percent full power using the autotransformer, and placing a target to 1.0 cm of the drop, and then rapidly turning the dial of the autotransformer to 75 percent full power the drop flies to the target, e.g., a grounded human finger.

In another related syringe version with the same device, the plunger is manually or depressed with a stepper motor continuously as the autotransformer is at 100% full scale and a fine spray results on the target.

In a capillary embodiment of this technology a fused silica capillary is placed into a vial that contains a liquid. The vial is placed on a conductive surface which is taken to a large positive potential (e.g. 15 kV) and the tip of the capillary is placed within one cm of ground potential which is physically lower in height form the height of the liquid in the vial, whereupon the liquid begins to spray at a very precise rate without faradaic processes.

In a related syringe embodiment, of the same device the liquid is optionally inductively charged briefly and then conductively using a direct wire to conducting surface like the syringe plunger to effect inductive, conductive liquid sample movement.

In a related version of the a similar device modified to have a coaxial non-conducting cylindrical shield extend over the end of the syringe barrel, and up to the end of the drops location, it is found upon depressing the plunger of an energized system that the spray is not created, but rather a drop remains for subsequent launching to a grounded target like a MALDI plate (ABI/MDS Sciex, CA) upon energizing same and pointing it to close to (e.g., a few cm) to ground.

In another embodiment of the device a twenty-four channel peristaltic pump (Idexcorp., Chicago Ill.) has its 24 lines brought to 24 PEEK unions and fitted with PEEK tubing such that standard 360 micron fused silica tubing of 150 micron ID can be joined thereto. This array is placed into a conducting plate with three lines of eight holes each row separated by 9 mm as per standard microtiter plate geometry with the tips of the capillaries being held on pipette tips, Plastibrand of Germany, 100 uL, above the ground plate by approximately 6 mm with a plate to plate distance of approximately 3.5 cm. The charge plate being connected to an American High Voltage (AHV) DC power supply system 200 watt power supply and the ground plate being connected to that device's electrical ground. The charging plate is connected to non-conductors connect it to a z axis robotic system and the ground plate being connected to a z axis robotic with each plate being 10 cm×25 cm×1 mm. Upon the ground plate, a microtiter plate is placed and secured by plastic chuck, Upon the initiation of the primed pump, the microtiter plate is moved under the 24 channels and at the appropriate time (e.g., 1, 2, 5 10, 20 seconds, as selected), the HV supply is energized, as the current is measured dropping the 24 drops into the microtiter plate. This is repeated two more times, and in seconds a 96 microtiter plates has had nanoliter, microliter or picoliter liquids placed into it without touching the container.

In yet another embodiment of this device that is identical to the immediately preceding example except that each line of the peristaltic pump is has a unique liquid or in another identical version of the same device using a 96 channel peristaltic pumping 96 different liquids where one dispense cycle can place 96 liquids into one microtiter plate with great rapidity.

In yet another embodiment of this class of devices, any glass vial with a septum lid containing a liquid can be charged by placement into a conducting or a non-conducting holder that is connected directly to an AHV system 100 watt programmable DC power supply. A tube (e.g., od 360×id 100 u fused silica) is placed into the liquid and out of the top of the vessel through a septa with an optional vent. The tube further goes into a stylus that can be handheld. With siphon flow initiated, the HV source can be turned on resulting in a extremely fine spray in the pL/sec regime that results from the when the tip is a cm or so from ground. Such sprays can be placed on paper placed on electronic ground. Alternatively, the same device can be employed to dispense liquids onto non-conductors when it is they that are the charged targets and when they are charged in a siphon or pump based system.

In an identical embodiment of the preceding example, the dispensing tube goes to a manifold with eight outputs that can place the same liquid in eight locales concurrently.

In one further embodiment the device is employed to send charged liquids into scientific instruments directly from LC columns without creating or with creating a spray where in the former mode, MS sensitivities are greatly increased as a great fraction of the analytical sample reaches the instrument; such as a mass spectrometer.

In another embodiment of the device a Spark Holland Alias liquid handling system (Spark Holland, Emmen, The Netherlands) is fitted with a DC, HV circuit that is presented herein (Version 3.0, 2.0 or 1.0) which has ECMO, HV −8.0 kV negative power supply and an EMCO 3 msec HV controlled relay switch and that is controlled via RS 232 interface and serial commands software present in the software attachment and a PC and their (Spark Holland) system software.

An inductor that is presented herein, is attached to their dispenser needle by the core part of the inductor, an Idexcorp, Upchurch Peek (Oak Harbor Wash.) union (e.g., a nano tight union or optionally a nanotight Y connector) which is fitted with 150 micron fused silica capillaries that are coated with Teflon (DuPont, DE) and placed a few millimeters above a typical MALDI (ABI/MDS Sciex, CA) plate.

Then with the syringe pump primed with the solvent of choice the program is run. This programs initializes the system, reprimes the pump and it positions the inductor ca. 2 mm above a test position on a MALDI plate where the pump is briefly energized for a few milliseconds, creating a small drop on the tip and immediately thereafter, or concurrently the inductor is taken to the user selected value energy value (e.g., −4.75 kV) in a user selected wave form (square pulse, exponential, quadratic,) effecting energy transfer to the liquid inductively to the capillary whereupon the liquid is charged, and it flies 2 mm (or it can go cms) onto the MALDI target, or alternatively into a microtiter plate or other targets. Next the platform is moved to present a fresh location or surface or optionally it is repeated for deposition and the process repeats for 24 dispenses in this case, Then the injector is moved to the next row and the process is repeated. This is accomplished until the 384 ABI, MALDI plate is filled. The same process can also be accomplished such that the z axis moves up and down with the sample tray movement and such that the drop energizing and firing is accomplished in unison to afford maximum force to the drop (i.e., inertial and the F=qE force.

In a variation of the above, the fused silica capillary can be replaced with a similar dimensioned fused silica capillary LC columns made with PRP1 (Hamilton Company, Reno Nev.) or any other material effecting LC column deposition when the automated Alias' LC valve is actuated and used to inject a liquids sample or other sample onto the LC column which parenthetically can be of other columns types, e.g., monolithic LC columns or for that matter the material in the column can be SPE media, media with antibodies, filters and other sample treatment of diverse types. In these operational modes where sample treatment is effected, direct deposition of the sample is made onto or into the target in millisecond timeframes, without any dead volume.

All or anyone of these devices can be placed into a fume or environmental chamber or faraday cage where humidity, particulate matter and all other variable including intrusion by electric fields of any type are minimized or all three to affect a controlled environment, and with various monitoring functions monitored by and integrated with a PC.

What is claimed is:

1. An induction based fluidic apparatus which is a) useful for accurately transporting or dispensing one liquid or for accurately transporting or dispensing a plurality of the same or different liquids, in similar or different microliter to femtoliter volume ranges, and optionally, b) is useful for performing one or more other operations concurrently or sequentially on the same or different liquids including those eluting from hybrid capillaries, pipettes, pipetted fitted syringes, pipetted fitted syringe or other pumps, pipette dispensers of all types fitted to SPE columns, HPLC, UPLC or other liquid treatment and instrument introduction pumps and devices with instrument, mass spectrometer sample introduction, and energizing same and sample placement devices; and furthermore which, c) is useful for accurately and precisely in both volumetric and spatial terms delivering treated liquids or liquids, drugs, anesthetics, taggants, slurries or cells, dissolved cells, suspended cells, biological fluids, DNA/RNA samples, glues, whole blood, paint, lubricants, viscous liquids, serum, semen, or suspended or other solids including nanoparticles to entities of all types including MALDI targets and microtiter plates, mass spectrometers and scientific instruments or all types, drugs or prescriptions, food, plants, animal and human subjects, packages or containers of all types, inanimate objects, and other objects either of a conductive, semi conductive or non-conductive material, rapidly, without touching same, and d) which is useful for manufacturing of 2D and 3D components such as charged functionalized solid entities or polymers or mixtures thereof, or non-charged polymers or pills, or wafers and or electronic or other components and e) which is useful for sample preparation for tissue MALDI, and LC/MALDI, LC/ESI/MS and LC/ESI/IMS and variants and for the characterization of bacteria by MALDI, SIMS or other energy/target systems and which is also useful for sample preparation and sample introduction and other testing related to medical diagnostics, disease and health biomarker testing via liquid processing to assess the condition of living or other systems which is comprised of: at least one air displacement pipette with at least one pipette tip reversibly attached to a terminal end of the said at least one pipette, and where said pipette tip has a side opening extending through a sidewall of the pipette tip, and where said pipette tip contains a compression fit capillary having geometry of precise, length, radii, shape and where said compression fit capillary has a polymeric coating on an outside and a polymeric coating on an inside of said compression fit capillary, and where the device further consists of at least one supporting Gaussian form fitting directing inductor where said inductor's terminal end is electrically connected to a form fitting area and where said inductor is connected via a flying lead to a switch and to an analogue or digital programmable bipolar HV power supply via another lead electrically connected to said switch, and where said bipolar HV power supply is connected via circuitry to a microprocessor or computer for control of said at least one power supply, and where the terminal end of said compression fit capillary is adjacent to a least one target which is electrically connected to said switch via a flying lead, and where an attached robotic system is connected with circuitry to said microprocessor or said computer for controlling the movement of said device.

2. A device of claim 1 further comprising the pipette tip with a side opening being conductive and that contains a compression fit capillary being made of precise length and radii and being coated with a polymer on the exterior thereof.

3. The device of claim 1 further comprising the pipette tip coated with a conductor with a side opening and that contains a compression fit capillary being made of pure materials of any kind and being of precise length and radii being coated on the upper part with a conductor and on the lower exterior part with non-conductor polymeric matter and optionally other polymeric material on the interior.

4. The device of claim 1 further comprising a holder or a stand that has at least one form fitting hole matching the shape of said pipette tips or other Gaussian surfaces, where said through hole contains a sharp cutting device embedded in the interior of said holder.

5. The device of claim 1 further comprising a non-conducting tube connected to an inductor with a flying lead whose opposite end is also connected to said inductor via a non-conducting tube with one end of said tube containing a precision length and radii and where a smaller tube with said non-conducting tube being connected to a resistance heating element connected to a power supply.

6. The device of claim 1 further comprising a non-conducting base with a three sided rectangular support sides where on said base within said sides, is a conducting surface with flying leads connected to a switch and where said support has top holders for the placement of at least one form fitting inductor in a support and where a conducting underside of said support is connected to said switch with flying leads and that to a foot pedal.

7. The device of claim 1 further comprising the pipette tip with a side opening where said tip contains a compression fit capillary being made of precise length and radii and being coated with a polymer on the exterior, and having a different polymer on the inside of said capillary where said capillary is color coded as to its length, radii, and contents.

8. The device of claim 1 further comprising a non-conductor slab with x by y rows of form fitting through holes where the underneath of said slab having said through holes is coated with conductive matter and said coating to flying leads, and where said block has thinner edges all around the circumference, and having at least one alignment hole on the edges of said slab.

9. The device of claim 1 further comprising a non-conducting variable radii tube cylinder having compression fit the terminal ends at both ends of said tube.

10. The device of claim 1 further comprising an array of conical conductive holes in a slab, on a holder having at it's base a conductor connected via flying leads to a current measurement device of any type connected by circuitry to the controlling microprocessor or computer.

11. A device of claim 1 further comprising the side opening of the pipette tip being a horizontal slit and that contains a compression fit capillary being made of precise length and radii and being coated with a polymer on the exterior of said device.

12. A device of claim 1 further comprising of a pipette tip with a side opening of any size or geometry that contains a compression fit capillary being made of precise length and radii and being coated with any polymer on the exterior and the interior of said device.

13. The device of claim 1 further comprising at least one holder with three smaller supports, having end holes centrally joined to a solid block of matter where at least one conical, or cylindrical inductor resides connected to at least one flying lead and a switch and connected to a HV power supply of any kind with another flying lead to a ground wire.

14. The device of claim 1 further comprising a flexible holder containing at least one strip where said holder has at least one cover and where said strip being further connected to a motor, a digital controller, and to a microprocessor or computer by circuitry for control of said strip.

15. The device of claim 1 further comprising the pipette tip with a side opening containing a compression fit capillary being of precise length and radii and being coated with a polymer on the exterior and the interior of said device, and where said devices of different geometry are marked with a different, unique color coded as to its volume.

16. The device of claim 1 further comprising the pipette tip with a side opening containing a compression fit capillary being made of precise length and radii and being coated with a polymer on the exterior and the interior of said device and where said capillary has further attached to it a zero dead volume union and that to another capillary of precise radii and length.

17. The device of claim 1 further comprising the pipette tip with a side opening containing a compression fit capillary being made of precise length and radii and being coated with a polymer on the exterior or the interior of said device and where the interior of said capillary contains fixed analyte capturing media.

18. The device of claim 1 further comprising the pipette tip with a side opening containing a compression fit capillary being made of precise length and radii and being color coated for different lengths and radii and containing volume marks along the length of said capillary and further having a polymer on the exterior and interior of said capillary.

19. The device of claim 1 further comprising the side opening being V shaped and where said tip contains a compression fit capillary being made of precise length and radii being color coated for different lengths and radii and containing volume marks along the length of said capillary and further having a polymer on the exterior and optionally on the interior of said capillary.

20. A method to dispense and measure liquid volumes shot into or onto targets using the device of claim 1 where the device further consists of a picoammeter or an electrometer connected to a switch via flying leads where said switch being further connected to a target where said target is further connected to a microprocessor or a controlling computer via circuitry and where said computer also controls a digital camera on a holder with feature identifying and pixel counting software on said computer and to a robotic x,y,z movement system for precise, programmed movement of said devices; comprising performing steps of energization of the said device such that droplets fly to said at least one targets as current measurements are made and as visual data are collected in said computer from said devices.

21. An inductive method for liquid sample introduction, charging and desolvation using the device of claim 1 where the device further consist of a heater in a conducting cylinder that is further contained in a closed non-conducting cylinder with a through hole on each end being located against an orifice of any scientific instrument, MALDI plate or other target where said non-conducting cylinder is further attached to gas fittings where said heater is further connect to via circuitry to a controlling microprocessor or computer; comprising performing steps of energization of the said device such that, liquid droplets are charged, launched to said target, and desolvated.

* * * * *